United States Patent
Gibson et al.

(10) Patent No.: US 6,812,236 B2
(45) Date of Patent: Nov. 2, 2004

(54) COMPOUNDS USEFUL IN THERAPY

(75) Inventors: Stephen Paul Gibson, Sandwich (GB); Ivan Tommasini, Sandwich (GB); David Morris Gethin, Sandwich (GB); Richard Edward Armer, Newhouse (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/108,160

(22) Filed: Mar. 27, 2002

(65) Prior Publication Data

US 2002/0099216 A1 Jul. 25, 2002

Related U.S. Application Data

(63) Continuation of application No. 09/575,951, filed on May 23, 2000, now abandoned.

(30) Foreign Application Priority Data

May 28, 1999 (GB) ............................................. 9912411

(51) Int. Cl.[7] ...................... C07D 211/00; A61K 31/445
(52) U.S. Cl. ....................................... 514/317; 546/192
(58) Field of Search .................. 514/357, 317; 546/337, 192

(56) References Cited

U.S. PATENT DOCUMENTS

| 4,081,450 A | 3/1978 | Zimmerman |
| 4,191,771 A | 3/1980 | Zimmerman |
| 4,292,321 A | 9/1981 | Pattison |
| 5,136,040 A | 8/1992 | Werner |
| 5,498,718 A | 3/1996 | Werner |
| 5,885,994 A | 3/1999 | Glase et al. |

FOREIGN PATENT DOCUMENTS

| DE | 4341403 | 6/1995 | |
| EP | 0007067 | 7/1979 | |
| EP | 0013078 | 7/1980 | |
| EP | 0136863 | 4/1985 | |
| EP | 0506468 A1 | 3/1992 | |
| EP | 0506468 B1 | 3/1992 | |
| EP | 0494717 | 8/1992 | |
| EP | 0287339 | 8/1994 | |
| EP | 0657428 | 6/1995 | |
| EP | 0506478 | 9/1997 | |
| EP | 0938898 | 9/1999 | |
| GB | 1525584 | 9/1978 | |
| GB | 2038812 | 7/1980 | |
| WO | WO 92/01672 | * 2/1992 | ......... C07D/211/18 |
| WO | 95/15327 | 6/1995 | |
| WO | 97/45419 | 12/1997 | |
| WO | 98/51311 | 11/1998 | |
| WO | 99/59971 | 11/1999 | |
| WO | 00/39089 | 7/2000 | |

OTHER PUBLICATIONS

Zimmerman, "Structure–Activity Relationship of Trans–3, 4–Dimethyl–4–(3–hydroxypheyl) Antagonists for $\mu$– and $\kappa$–Opioid Receptors", *J. Med. Chem.* 36:2833–2841 (1993).

Mitch, et al., "3,4–Dimethyl–4–(3–hydroxyphenyl) Piperidines: Opioid Antagonists with Potent Anorectant Activity", *J. Med. Chem.* 36:2842–2850 (1993).

Belliotti, et al., "Isoindolinone Enantiomers Having Affinity for the Dopamine D4 Receptor", *Bioorganic & Medicinal Chemistry Letters 8* 1499–1502 (1998).

* cited by examiner

Primary Examiner—Zinna Northington Davis
(74) Attorney, Agent, or Firm—Scully, Scott, Murphy & Presser

(57) ABSTRACT

There is provided a compound of formula I,

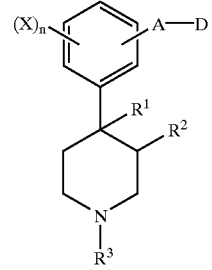

I wherein A, D, $R^1$, $R^2$, $R^3$, X and n have meanings given in the description, which are useful in the prophylaxis and in the treatment of diseases mediated by opiate receptors, such as pruritus.

14 Claims, No Drawings

COMPOUNDS USEFUL IN THERAPY

RELATED APPLICATION

This is a continuation of U.S. Ser. No. 09/575,951 filed on May 23, 2000 now abandond, which claims priority of Great Britain Application No. GB 9912411.7 filed on May 28, 1999.

FIELD OF THE INVENTION

This invention relates to pharmaceutically useful compounds, in particular compounds that bind to opiate receptors (e.g. mu, kappa and delta opioid receptors).

BACKGROUND OF THE INVENTION

Compounds that bind to such receptors are likely to be useful in the treatment of diseases mediated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction, sexual dysfunction, shock, stroke, spinal damage and head trauma.

There is a particular need for an improved treatment of itching. Itching, or pruritus, is a common dermatological symptom that can give rise to considerable distress in both humans and animals. Pruritus is often associated with inflammatory skin diseases which may be caused by hypersensitivity reactions, including reactions to insect bites, such as flea bites, and to environmental allergens, such as house dust mite or pollen; by bacterial and fungal infections of the skin; or by ectoparasite infections.

Existing treatments that have been employed in the treatment of pruritus include the use of corticosteroids and antihistamines. However, both of these treatments are known to have undesirable side effects. Other therapies that have been employed include the use of essential fatty acid dietary supplements, though these have the disadvantages of being slow to act, and of offering only limited efficacy against allergic dermatitis. A variety of emollients such as soft paraffin, glycerine and lanolin are also employed, but with limited success.

Thus, there is a continuing need for alternative and/or improved treatments of pruritus.

Certain 4-arylpiperidine-based compounds are disclosed in inter alia European patent applications EP 287339, EP 506468, EP 506478 and *J. Med. Chem.* 1993, 36, 2833–2850 as opioid antagonists. In addition, International Patent Application WO 95/15327 discloses azabicycloalkane derivatives useful as neuroleptic agents.

SUMMARY OF THE INVENTION

According to the invention there is provided compounds of formula I:

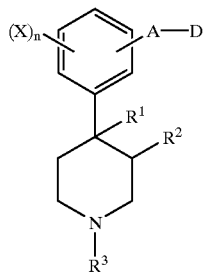

I wherein A represents a single bond, $C_{1-4}$ alkylene, $C_{2-4}$ alkenylene or $C_{2-4}$ alkynylene, which alkylene, alkenylene or alkynylene groups are optionally substituted by one or more substituents selected from $C_{1-4}$ alkyl, $C_{1-4}$ alkoxy, halo or OH;

D represents H, OH, CN, $N(R^4)(R^5)$, $N(H)R^6$, $C(O)N(R^4)(R^5)$, $C(O)OR^7$, $C(O)R^8$, $C(=NR^{9a})R^8$, or $C(=NOR^{9b})R^8$; provided that when A represents $C_{2-4}$ alkenylene or $C_{2-4}$ alkynylene, and D represents OH, $N(R^4)(R^5)$ or $N(H)R^6$, then D is not directly attached to an unsaturated carbon atom;

and provided that when A represents a single bond, then D does not represent H, OH, $N(R^4)(R^5)$ or $N(H)R^6$;

$R^4$ and $R^5$ independently represent H, $C_{1-6}$ alkyl, $C_{3-8}$ cycloalkyl, aryl, $C_{1-4}$ alkylphenyl, which latter four groups are optionally substituted by one or more substituents selected from nitro, halo, $C_{1-4}$ alkyl or $C_{1-4}$ alkoxy (which latter two groups are optionally substituted by one or more halo atoms), or $R^4$ and $R^5$, together with the N-atom to which they are attached, form a 4- to 7-membered heterocyclic ring, which ring optionally contains one or more additional heteroatoms selected from oxygen, nitrogen and sulfur and which ring is optionally substituted by one or more substituents selected from $C_{1-4}$ alkyl, $C_{1-4}$ alkoxy, OH, =O, nitro, amino or halo;

$R^6$ represents $C(O)R^{10a}$, $C(O)OR^{10b}$ or $S(O)_2R^{10c}$;

$R^{10a}$ to $R^{10c}$ independently represent $C_{1-4}$ alkyl, $C_{3-8}$ cycloalkyl, aryl, $C_{1-4}$ alkylphenyl (which four groups are all optionally substituted by or one or more substituents selected from nitro, halo, $C_{1-4}$ alkyl or $C_{1-4}$ alkoxy (which latter two groups are optionally substituted by one or more halo atoms)), or $R^{10a}$ represents H;

$R^7$ and $R^8$ independently represent H, $C_{1-6}$ alkyl, $C_{3-8}$ cycloalkyl, aryl or $C_{1-4}$ alkylphenyl, which latter four groups are optionally substituted by one or more substituents selected from nitro, halo, $C_{1-4}$ alkyl or $C_{1-4}$ alkoxy (which latter two groups are optionally substituted by one or more halo atoms);

$R^{9a}$ and $R^{9b}$ independently represent $C_{1-6}$ alkyl, $C_{3-8}$ cycloalkyl, aryl, $C_{1-4}$ alkylphenyl, which latter four groups are optionally substituted by one or more substituents selected from nitro, halo, $C_{1-4}$ alkyl or $C_{1-4}$ alkoxy (which latter two groups are optionally substituted by one or more halo atoms), or $R^{9b}$ represents H;

$R^1$ and $R^2$ are each independently H or $C_{1-4}$ alkyl;

$R^3$ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $—N(R^{11a})(R^{11b})$), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{11c}$, $S(O)_pR^{11d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{12a})S(O)_2R^{13}$, Het$^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $—W—A^1—N(R^{12b})(R^{12c})$;

p is 0, 1 or 2;

W represents a single bond, C(O) or $S(O)_q$;

$A^1$ represents a single bond or $C_{1-10}$ alkylene;

provided that when both W and $A^1$ represent single bonds, then the group —$N(R^{12b})(R^{12c})$ is not directly attached to an unsaturated carbon atom;

q is 0, 1 or 2;

$R^{11a}$ to $R^{11d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{11d}$ does not represent H when p represents 1 or 2;

$R^{12a}$ to $R^{12c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^3$, or $R^{12b}$ and $R^{12c}$ together represent unbranched $C_{2-6}$ alkylene which alkylene group is optionally interrupted by O, S and/or an $N(R^{14})$ group and is optionally substituted by one or more $C_{1-4}$ alkyl groups;

$R^{13}$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

$R^{14}$ represents H, $C_{1-6}$ alkyl, $C_{3-8}$ cycloalkyl, $A^2$-($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

X is H, halo, $C_{1-4}$ alkyl or $C_{1-4}$ alkoxy (which latter two groups are optionally substituted by one or more halo atoms);

n is 0, 1 or 2;

or pharmaceutically, or veterinarily, acceptable derivatives thereof; which compounds are referred to together hereinafter as "the compounds of the invention."

DETAILED DESCRIPTION OF THE INVENTION

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_{1-4}$ alkyl, $C_{1-4}$ alkoxy $C_{1-4}$ alkoxy carbonyl and $C_{1-5}$ alkanoyl (which latter four groups are optionally substituted by one or more halo atoms).

The heterocyclic rings that $Het^1$, $Het^2$ and $Het^3$ represent and that $N(R^4)(R^5)$ may represent, may be fully saturated, partially unsaturated and/or wholly or partially aromatic in character.

For the avoidance of doubt, when heterocyclic groups (i.e. $Het^1$, $Het^2$, $Het^3$ and some definitions of $N(R^4)(R^5)$) are at least part-saturated, possible points of substitution include the atom (e.g. the carbon atom) at the point of attachment of the heterocyclic group to the rest of the Molecule. Het ($Het^1$, $Het^2$ and $Het^3$) groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All heterocyclic groups (i.e. $Het^1$, $Het^2$, $Het^3$ and some definitions of N(R)(R)) may also be in N- or S-oxidized forms.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succinic, tartaric, cinnamic, ascorbic and related acids; base addition salts; salts formed with bases, for example, the sodium, potassium and $C_{1-4}$ alkyl ammonium salts.

The compounds of the invention may also be in the form of quaternary ammonium salts, e.g. at the piperdine moiety, which salts may be formed by reaction with a variety of alkylating agents, such as an alkyl halide or an ester of sulfuric, or an aromatic sulfonic, acid.

The compounds of the invention may exhibit tautomerism. All tautomeric forms of the compounds of formula I are included within the scope of the invention.

The compounds of the invention contain one or more asymmetric centres and thus they can exist as enantiomers and diastereomers. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers.

Also included within the scope of the invention are radiolabelled derivatives of compounds of formula I which are suitable for biological studies.

Preferred compounds of the invention include those wherein:

The group A-D is attached in the meta-position relative to the piperidine ring;

$R^1$ represents $C_{1-2}$ alkyl;

$R^2$ represents H or $C_{1-2}$ alkyl;

$R^3$ represents saturated $C_{1-10}$ (e.g. $C_{1-8}$) alkyl, optionally substituted by one or more substituents selected from $OR^{11c}$, CN, halo, $C_{2-4}$ alkanoyl, $C_{1-4}$ alkoxy carbonyl, $N(R^{12a})SO_2R^{13}$, $Het^1$, aryl (which latter group is optionally substituted by one or more substituents selected from OH, $C_{1-4}$ alkyl, $C_{1-4}$ alkoxy, $C_{2-5}$ alkanoyl, halo, nitro, amino, CN and $CONH_2$), or —W—$A^1$—$N(R^{12b})(R^{12c})$;

$R^{11c}$ represents H, $C_{1-6}$ alkyl or aryl (which latter groups is optionally substituted by one or more substituents selected from OH, $C_{1-4}$ alkyl, $C_{1-4}$ alkoxy, $C_{2-5}$ alkanoyl, halo, nitro, amino, CN and $CONH_2$);

$R^{12a}$ to $R^{12c}$ independently represent H, $C_{1-4}$ alkyl, $C_{1-2}$ alkylphenyl or aryl (which latter three groups are optionally substituted by one or more substituents selected from halo, $C_{1-4}$ alkyl or $C_{1-4}$ alkoxy);

$R^{13}$ represents $C_{1-4}$ alkyl, $C_{1-2}$ alkylphenyl or aryl (which three groups are all optionally substituted by one or more substituents selected from halo, $C_{1-4}$ alkyl or $C_{1-4}$ alkoxy);

W represents C(O);

$A^1$ represents a single bond.

More preferred compounds of the invention include those wherein:

A represents a single bond, $C_{1-4}$ alkylene, $C_{2-4}$ alkenylene or $C_{2-4}$ alkynylene, which alkylene, alkenylene or alkynylene groups are optionally substituted by one or more OH and/or methyl groups;

D represents H, OH, CN, $N(H)R^4$, $N(H)C(O)R^{10a}$, $N(H)C(O)OR^{10b}$, $N(H)S(O)_2R^{10c}$, $C(O)N(R^4)(R^5)$, $C(O)OR^7$, $C(O)R^8$ or $C(=NOH)R^8$;

$R^4$ and $R^5$ independently represent H, $C_{1-4}$ alkyl or $C_{1-3}$ alkylphenyl (which latter two groups are both optionally substituted by $C_{1-4}$ alkoxy);

$R^7$ and $R^8$ independently represent H or $C_{1-4}$ alkyl;

$R^{10a}$ to $R^{10c}$ independently represent $C_{1-4}$ alkyl (optionally substituted by one or more halo atoms);

$R^1$ represents methyl;

$R^2$ represents H or methyl;

$R^3$ represents saturated $C_{1-7}$ alkyl, optionally substituted by one or more substituents selected from CN, $OR^{11c}$ or phenyl;

$R^{11c}$ represents C, alkyl or phenyl;

X represents halo, particularly fluoro;

n represents 1 or, preferably, 0.

Particularly preferred compounds of the invention include those wherein:

A represents a single bond, —$CH_2$—, —$CH(CH_3)$—, —$C(CH_3)_2$—, —CH(OH)—, —$(CH_2)_2$—, —CH=CH—, or —C≡C—;

D represents H, OH, CN, $NH_2$, $N(H)CH_3$, CHO, CH(=NOH), $C(O)CH_3$, $CO_2CH_3$, $CO_2H$, $C(O)NH_2$, $C(O)N(H)CH_3$, $C(O)N(H)Et$, $C(O)N(H)(2\text{-MeOEt})$, $C(O)N(H)n\text{-Pr}$, $C(O)N(H)i\text{-Pr}$, $C(O)N(H)n\text{-Bu}$, $C(O)N(H)i\text{-Bu}$, $C(O)N(H)t\text{-Bu}$, $C(O)N(H)CH_2Ph$, $C(O)N(CH_3)_2$, $C(O)N(Et)_2$, $N(H)C(O)CH_3$, $N(H)C(O)OCH_3$, $N(M)S(O)_2CH_3$ or $N(H)S(O)_2CF_3$;

$R^1$ and $R^2$ represent methyl groups in the mutually trans configuration;

$R^3$ represents benzyl, 5-cyanopentyl, n-hexyl, 5-methylhexyl, 2-phenoxyethyl or 3-phenylpropyl.

Preferred compounds of the invention include the compounds of the Examples described hereinafter.

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I in which A represents $C_{2-4}$ alkynylene (in which group the carbon-carbon triple bond is $\alpha,\beta$ to the benzene ring), which alkynylene group is optionally substituted at the 3- and/or the 4-C (relative to the benzene ring) by one or more substituents defined hereinbefore in respect of A, and/or one of the groups defined hereinbefore in respect of D, or (when D is not attached at the 3- or 4-C) which alkynylene group is substituted at the 2-C (relative to the benzene ring) by CN, $C(O)N(R^4)(R^5)$, $C(O)OR^7$, $C(O)R^8$, $C(=NR^{9a})R^8$, or $C(=NOR^{9b})R^8$, may be prepared by reaction of a corresponding compound of formula II,

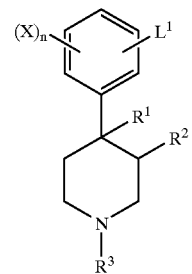

II wherein $L^1$ is a suitable leaving group such as halogen, preferably bromine or iodine, or a sulfonate such as trifluoromethanesulfonate, and $R^1$, $R^2$, $R^3$, X and n are as hereinbefore defined, with a compound of formula III,

III

M≡≡≡—$A^3$—D wherein M represents (as appropriate) H, a tin-containing moiety (e.g. tributylstannyl), a boron derivative (e.g. a boronic acid), a zinc halide, a magnesium halide or an alkali metal (which latter three groups may be formed in situ from the corresponding halide), $A^3$ represents a single bond or $C_{1-2}$ alkylene (optionally substituted by one or more substituents selected from $C_{1-4}$ alkyl, $C_{1-4}$ alkoxy, OH or halo), and D is as hereinbefore defined, provided that when $A^3$ represents a single bond, then D does not represent H, OH, $N(R^4)(R^5)$ or $N(H)R^6$, wherein $R^4$, $R^5$ and $R^6$ are as hereinbefore defined, for example at between room and reflux temperature in the presence of a suitable catalyst system (e.g. bis(triphenylphosphine)palladium(II) chloride combined with copper(I) iodide) and an appropriate organic base (e.g. triethylamine).

2. Compounds of formula I in which A represents $C_{2-4}$ alkenylene (in which group the carbon-carbon double bond is $\alpha,\beta$ to the benzene ring), which alkenylene group is optionally substituted at the 2-C (relative to the benzene ring) by $C_{1-4}$ alkyl, and also optionally substituted at the 3- and/or 4-C (relative to the benzene ring) by one or more of the substituents defined hereinbefore in respect of A and/or one of the groups defined hereinbefore in respect of D, or which alkenylene group is substituted at the 2-C (relative to the benzene ring) by CN, C(O)N(R$^4$)$^5$, C(O)OR$^7$, C(O)R$^8$, C(=NR$^{9a}$)R$^8$, or C(=NOR$^{9b}$)R$^8$, may be prepared by reaction of a corresponding compound of formula II, as hereinbefore defined, with a compound of formula IV,

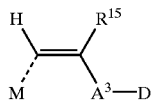

IV wherein the dashed bond represent optional cis- or trans-geometry, R$^{15}$ represents H or C$_{1-4}$ alkyl, and A$^3$, D and M are as hereinbefore defined, for example at between room temperature and reflux temperature in the presence of a reaction-inert solvent (e.g. 1,4dioxan. or THF), an appropriate catalyst (e.g. tetrakis(triphenylphosphine)palladium (0) or bis(triphenylphosphine)palladium(II) acetate) and either (as appropriate) a suitable source of halide ion (e.g. lithium chloride) or a suitable base (e.g. triethylamine).

3. Compounds of formula I in which A represents a single bond and D represents CN may be prepared by reaction of a compound of formula V,

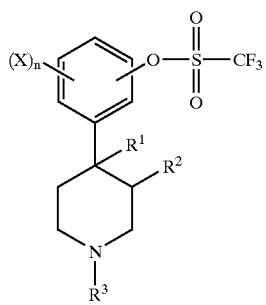

V wherein R$^1$, R$^2$, R$^3$, X and n are as hereinbefore defined with an alkali metal cyanide (e.g. potassium cyanide), for example at raised temperature in the presence of a reaction-inert solvent (e.g. N-methylpyrrolidine) and a suitable catalyst (e.g. palladium(II) acetate combined with 1,1'-bis(diphenylphosphino)ferrocene).

Compounds of formula V may be prepared by reaction of a corresponding compound of formula VI,

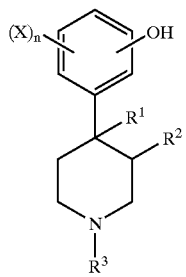

VI wherein R$^1$, R$^2$, R$^3$, X and n are as hereinbefore defined, with an appropriate triflating agent (e.g. N-phenyltri-fluoromethanesulfonimide), for example at between 0° C. and room temperature in the presence of a reaction-inert organic solvent (e.g. dichloromethane) and a suitable base (e.g. triethylamine).

Compounds of formula VI may be prepared by reaction of a corresponding compound of formula VII,

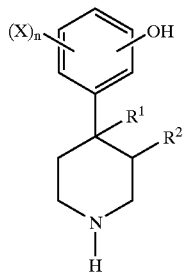

VII in which R$^1$, R$^2$, X and n are as hereinbefore defined, with a compound of formula VIII, $$R^3—L^1 \quad \text{VIII}$$

wherein R$^3$ and L$^1$ are as hereinbefore defined, under conditions that are known to those skilled in the art, which include, for example, alkylation at between room temperature and reflux temperature in the presence of a reaction-inert organic solvent (e.g. N,N-dimethylformamide) and a suitable base (e.g. NaHCO$_3$), and arylation at between room temperature and reflux temperature in the presence of a suitable catalyst system (e.g. tris(dibenzylideneacetone) palladium(0) combined with tri-o-tolylphosphine), an appropriate strong base (e.g. sodium tert-butoxide) and a reaction-inert solvent (e.g. toluene).

4. Compounds of formula I in which A represents C$_{1-4}$ alkylene, C$_{2-4}$ alkenylene or C$_{2-4}$ alkynylene, which alkylene, alkenylene or alkynylene groups are optionally substituted by one or more substituents selected from C$_{1-4}$ alkyl, C$_{1-4}$ alkoxy, halo or OH, and D represents NH$_2$ (which is attached to a CH$_2$ group) may be prepared by reduction of a; corresponding compound of formula I in which A represents (as appropriate) a single bond, C$_{1-3}$ alkylene, C$_{2-3}$ alkenylene or C$_{2-3}$ alkynylene, which alkylene, alkenylene or alkynylene groups are optionally substituted by one or more substituents selected from C$_{1-4}$ alkyl, C$_{1-4}$ alkoxy, halo or OH, and D represents CN, for example at between room and reflux temperature in the presence of a suitable reducing agent (e.g. lithium aluminium hydride) and an appropriate solvent (e.g. THF).

5. Compounds of formula I in which D represents C(O)NH$_2$ may be prepared by controlled hydrolysis of a corresponding compound of formula I in which D represents CN, for example by reaction with polyphosphoric acid at between 50 and 150° C.

6. Compounds of formula I in which A represents a single bond and D represents C(O)—(C$_{1-6}$ alkyl) or C(O)—(C$_{1-4}$ alkylphenyl), which alkyl and alkylphenyl groups are both optionally substituted by one or more of the substituents defined hereinbefore in respect of R$^8$, may be prepared by hydrolysis of a corresponding compound of formula IX,

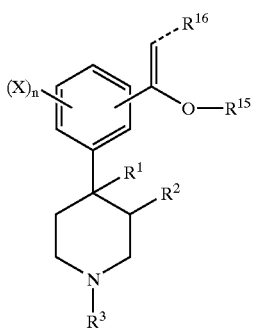

IX wherein $R^{15}$ represents $C_{1-6}$ alkyl, $R^{16}$ represents H, $C_{1-5}$ alkyl, phenyl or $C_{1-3}$ alkylphenyl which latter three groups are all optionally substituted by one or more substituents selected from nitro, halo, $C_{1-4}$ alkyl or $C_{1-4}$ alkoxy (which latter two groups are optionally substituted by one or more halo atoms), the dashed bond indicates optional cis- or trans-geometry, and $R^1$, $R^2$, $R^3$, X and n are as hereinbefore defined, for example under conditions known to those skilled in the art (e.g. by reaction at between room and reflux temperature with an aqueous solution of a mineral acid).

Compounds of formula IX may be prepared by reaction of a compound of formula II, as hereinbefore defined, with a compound of formula X,

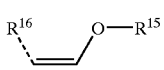   X wherein the dashed bond indicates optional cis- or trans-geometry, and $R^{15}$ and $R^{16}$ are as hereinbefore defined, for example at between room temperature and reflux temperature in the presence of an appropriate catalyst (e.g. palladium(II) acetate combined with 1,1'-bis (diphenylphosphino)ferrocene), an organic base (e.g. triethylamine) and an appropriate solvent (e.g. N,N-dimethylformamide).

7. Compounds of formula I in which D represents C(O)$R^8$, wherein $R^8$ is as hereinbefore defined provided that it does not represent H, may be prepared by reaction of a corresponding compound of formula I in which D represents CN with an organometallic compound capable of delivering an $R^{8a}$-containing anion (e.g. an appropriate organolithium or Grignard reagent), wherein $R^{8a}$ is defined as for $R^8$ above provided that it does not represent H, for example at between −80 and 10° C. in the presence of a reaction-inert organic solvent (e.g. tetrahydrofuran).

8. Compounds of formula I in which A represents a single bond and D represents C(O)O$R^7$, wherein $R^7$ is as hereinbefore defined provided that it does not represent H, may be prepared by reaction of a corresponding compound of formula V, as hereinbefore defined, with carbon monoxide and an alcohol of formula $R^{7a}$OH, wherein $R^{7a}$ is defined as for $R^7$ above provided that it does not represent H, for example in the presence of a suitable transition-metal catalyst system (e.g. palladium(II) acetate combined with 1,1'-bis (diphenylphosphino)ferrocene) and a reaction-inert solvent (erg. DMF).

9. Compounds of formula I in which A represents $C_{1-4}$ alkylene, $C_{2-4}$ alkenylene or $C_{2-4}$ alkynylene, which alkylene, alkenylene or alkynylene groups are optionally substituted by one or more substituents selected from $C_{1-4}$ alkyl, $C_{1-4}$ alkoxy, halo or OH, and D represents OH (which is attached to a $CH_2$ group) may be prepared by reduction of a corresponding compound of formula I in which A represents (as appropriate) a single bond, $C_{1-3}$ alkylene, $C_{2-3}$ alkenylene or $C_{2-3}$ alkynylene, which alkylene, alkenylene or alkynylene groups are optionally substituted by one or more substituents selected from $C_{1-4}$ alkyl, $C_{1-4}$ alkoxy, halo or OH, and D represents C(O)O$R^{7a}$, wherein $R^{7a}$ is as hereinbefore defined, for example at between 0° C. and reflux temperature in the presence of a suitable reducing agent (e.g. lithium aluminium hydride) and an appropriate solvent (e.g. THF).

10. Compounds of formula I in which A represents $C_{1-4}$ alkylene, $C_{2-4}$ alkenylene or $C_{2-4}$ alkynylene, which alkylene, alkenylene or alkynylene groups are gem-disubstituted with two $C_{1-4}$ alkyl groups (a to D) and are optionally substituted by one or more further substituents selected from $C_{1-4}$ alkyl, $C_{1-4}$ alkoxy, halo or OH, and D represents OH, may be prepared by reaction of a corresponding compound of formula I in which A represents (as appropriate) a single bond, $C_{1-3}$ alkylene, $C_{2-3}$ alkenylene or $C_{2-3}$ alkynylene, which alkylene, alkenylene or alkynylene groups are optionally substituted by one or more substituents selected from $C_{1-4}$ alkyl, $C_{1-4}$ alkoxy, halo or OH, and D represents C(O)O$R^{7a}$, wherein $R^{7a}$ is as hereinbefore defined, with a suitable $C_{1-4}$ alkyl-delivering organometallic compound (e.g. an alkylmagnesium halide), for example at between −10° C. and reflux temperature in the presence of a suitable solvent (e.g. THF).

11. Compounds of formula I in which D represents C(O)N($R^4$)($R^5$), wherein $R^4$ and $R^5$ are as hereinbefore defined, may be prepared by reaction of a corresponding compound of formula I in which D represents C(O)O$R^{7a}$, and $R^{7a}$ is as hereinbefore defined, with a compound of formula XI,

HN($R^4$)($R^5$)   XI or an acid (e.g. HCl) addition salt thereof, wherein $R^4$ and $R^5$ are as hereinbefore defined, for example at a temperature of between −10 and +150° C. and a pressure of between 1 and 10 atmospheres, optionally in the presence (as appropriate) of a Lewis-acidic catalyst (e.g. trimethylaluminium) and a reaction-inert solvent (e.g. toluene).

12. Compounds of formula I in which D represents C(O)N($R^4$)($R^5$), wherein $R^4$ and $R^5$ are as hereinbefore defined, may alternatively be prepared by reaction of a corresponding compound of formula I in which D represents C(O)OH with a compound of formula XI, as hereinbefore defined, under coupling conditions known to those skilled in the art.

13. Compounds of formula I in which D represents C(O)OH may be prepared by hydrolysis of a corresponding compound of formula I in which D represents C(O)O$R^{7a}$, wherein $R^{7a}$ is as hereinbefore defined, under conditions that are known to those skilled in the art.

14. Compounds of formula I in which D represents N(H)$R^6$, wherein $R^6$ is as hereinbefore defined, may be prepared by reaction of a corresponding compound of formula I in which D represents $NH_2$ with a compound of formula XII,

   XII wherein $R^6$ and $L^1$ are as hereinbefore defined, for example under conditions that are known to those skilled in the art, which include reaction at between −10° C. and reflux temperature in the presence of a suitable base (e.g. triethylamine or pyridine) and, optionally, a reaction-inert solvent (e.g. THF or dichloromethane).

15. Compounds of formula I in which A represents $C_{1-4}$ alkyl and D represents $N(R^4)(^5)$ or $N(H)C(O)R^{10a}$ attached at the 1-, 2- or 3-C (relative to the benzene ring), wherein $R^4$, $R^5$ and $R^{10a}$ are as hereinbefore defined, may be prepared by reaction of a corresponding compound of formula I in which A represents $C_{1-4}$ alkenylene unsaturated α,β-, β,γ- or γ,δ-(respectively) relative to the benzene ring and D represents H, with a compound of formula XI, as hereinbefore defined, or a compound of formula XIII,

    XIII wherein $R^{10a}$ is as hereinbefore defined, for example at between −10° C. and room temperature in the presence of a suitable mercury(II) salt (e.g. mercury(II) acetate, trifluoroacetate, nitrate, or perchlorate), optionally in the presence of a reaction-inert solvent (e.g. THF), and followed by in situ reduction of the mercury adduct by the addition of a suitable hydride-delivering agent (e.g. sodium borohydride), optionally in the presence of water.

16. Compounds of formula I in which A represents $C_{2-4}$ alkylene optionally substituted by one or more substituents selected from $C_{1-4}$ alkyl, $C_{1-4}$ alkoxy, halo or OH, and D represents OH may be prepared by oxidation of a corresponding borane adduct of formula XIV,

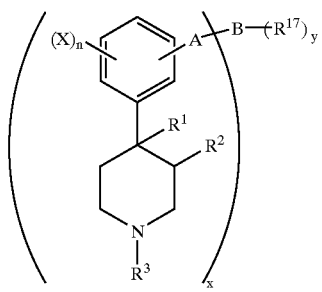

XIV wherein x is 1, 2 or 3, y is (as appropriate) (3-x) or 1, $R^{17}$ is (as appropriate) H, halo, an alkyl, or a cycloalkyl group providing one or two bonds to boron (e.g. disiamyl or thexyl), A represents (as appropriate) $C_{2-4}$ alkylene optionally substituted by one or more substituents selected from $C_{1-4}$ alkyl, $C_{1-4}$ alkoxy, halo or OH, and $R^1$, $R^2$, $R^3$, X and n are as hereinbefore defined, for example by reaction with a tertiary amine N-oxide (e.g. trimethylamine N-oxide) at between room and reflux temperature in the presence of a reaction-inert solvent (e.g. THF or a THF/diglyme mixture).

The skilled person will appreciate that, in compounds of formula XIV, bonds between boron atoms and piperidine N-atoms may be present.

Compounds of formula XIV may be prepared by reaction of a corresponding compound of formula I in which A represents (as appropriate) $C_{2-4}$ alkenylene optionally substituted by one or more substituents selected from $C_{1-4}$ alkyl, $C_{1-4}$ alkoxy, halo or OH, and D represents H with borane or a suitable derivative thereof (e.g. thexylborane, disiamylborane or 9-borabicyclo[3.3.1]nonane), for example at between −10° C. and room temperature in the presence of a suitable solvent (e.g. THF or a THF/diglyme mixture).

17. Compounds of formula I in which A represents a $C_{2-4}$ alkylene group substituted (α to D) with an OH group and D represents OH may be prepared by reaction of a corresponding compound of formula I in which A represents a $C_{2-4}$ alkenylene group and D represents H with a suitable dihydroxylating reagent (e.g. sub-stoichiometric $OsO_4$ combined with 4-methylmorpholine N-oxide), for example at between 0° C. and reflux temperature in the presence of a reaction-inert solvent (e.g. a water/acetone mixture).

18. Compounds of formula I in which A represents a single bond or a $C_{1-2}$ alkylene group (as appropriate) and D represents C(O)H may be prepared by reaction of a corresponding of formula I in which A represents a $C_{2-4}$ alkylene group substituted (α to D) with an OH group and D represents OH with a reagent that effects 1,2-diol oxidative cleavage (e.g. sodium periodate).

19. Compounds of formula I in which D represents $C(=NR^{9a})R^8$ or $C(=NOR^{9b})R^8$, wherein $R^8$, $R^{9a}$ and $R^{9b}$ are as hereinbefore defined, may be prepared by reaction of a corresponding compound of formula I in which D represents $C(O)R^8$ with a compound of formula XV,

    XV or a compound of formula XVI,

    XVI wherein $R^{9a}$ and $R^{9b}$ are as hereinbefore defined, for example under conditions that are known to those skilled in the are, which include reaction at between room and reflux temperature in the presence of a suitable solvent (e.g. a lower alkyl alcohol such as methanol or ethanol).

20. Compounds of formula I in which A represents $C_{1-4}$ alkylene substituted (α to D) with an OH group and D represents $N(H)CH_3$ (at the alkylene chain terminus) may be prepared by reduction of a corresponding compound of formula XVII,

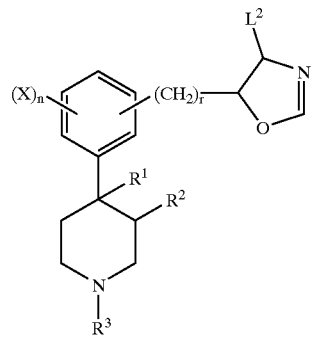

XVII wherein r is 0, 1 or 2, $L^2$ represents H or a group capable, when attached to a $C_2$ alkylene unit, of undergoing 1,2-elimination (relative to the $L^2$ group, e.g. an alkyl or aryl sulfoxide or sulfone), and $R^1$, $R^2$, $R^3$, X and n are as hereinbefore defined, for example, at between −10° C. and reflux temperature in the presence of a suitable reducing agent (e.g. lithium aluminium hydride) and a reaction-inert solvent (e.g. THF).

Compounds of formula XVII may be prepared by reaction of a corresponding compound of formula I in which A represents a single bond or $C_{1-2}$ alkylene and D represents C(O)H with a compound of formula XVIII,

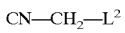    XVIII wherein $L^2$ is as hereinbefore defined, for example at between 0° C. and reflux temperature in the presence of a suitable solvent (e.g. ethanol) and a catalytic quantity of a cyanide salt (e.g. sodium cyanide).

21. Compounds of formula I wherein $R^3$ represents $C_1$ alkyl optionally substituted by $C_{3-8}$ cycloalkyl, $Het^1$, aryl, adamantyl, (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified hereinbefore in respect to $R^3$), which alkyl, alkenyl or alkynyl groups are attached to the piperidine nitrogen atom via a $CH_2$ group, wherein $Het^1$ is as hereinbefore defined, may be prepared by reduction of a corresponding compound of formula XIX,

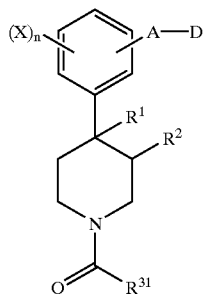

XIX wherein $R^{31}$ represents H, $C_{3-8}$ cycloalkyl, $Het^1$, aryl, adamantyl, (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{11c}$, $S(O)_pR^{11d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^1)S(O)_2R^{13}$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or —W—$A^1$—$N(R^{12b})(R^{12c})$ and $R^1$, $R^2$, $R^{11c}$, $R^{11d}$, $R^{12a}$ to $R^{12c}$, $R^{13}$, H W, X, $A^1$, A and D are as hereinbefore defined, using a suitable reducing agent (e.g. lithium aluminium hydride or a borane derivative), for example as described hereinbefore.

The skilled person will appreciate that this reduction may take place simultaneously with other reduction steps described herein (see, for example, processes 4, 9 and 16).

Compounds of formula XIX may be prepared by reaction of a corresponding compound of formula XX,

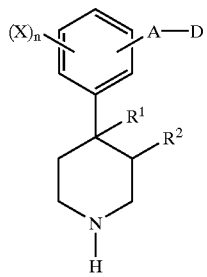

XX wherein $R^1$, $R^2$, A, D, X and n are as hereinbefore defined with a compound of formula XXI, $$R^{31}CO_2H \quad \text{XXI}$$

or a suitable (e.g. carboxylic acid) derivative thereof (e.g. an acid halide or anhydride), wherein $R^{31}$ is as hereinbefore defined, using coupling conditions known to those skilled in the art.

Compounds of formulae XIX and XX may be prepared from appropriate precursors by analogy with methods, disclosed hereinbefore that describe the preparation of compounds of formula I.

22. Compounds of formula I may be prepared by reaction of a corresponding compound of formula XX, as hereinbefore defined, with a compound of formula VIII, as hereinbefore defined, under conditions that are well known to those skilled in the art, for example as described hereinbefore in respect of the production of compounds of formula VI.

23. Compounds of formula I wherein $R^3$ represents $C_1$ alkyl, which, in place of being optionally substituted by the substituents as defined hereinbefore, is instead optionally substituted by $R^{31}$, wherein $R^{31}$ is as hereinbefore defined, may be prepared by reaction of a corresponding compound of formula XX, as hereinbefore defined, with a compound of formula XXII, $$R^{31}CHO \quad \text{XXII}$$

wherein $R^{31}$ is as hereinbefore defined, for example in the presence of a suitable reducing agent (e.g. sodium borohydride, sodium cyano-borohydride or sodium triacetoxyborohydride) and an appropriate solvent (e.g. methanol).

24. Compounds of formula I wherein $R^3$ is a $C_{1-10}$ alkyl, $C_{4-10}$ alkenyl or $C_{4-10}$ alkynyl group that is fully saturated from 1- to 3-C (relative to the piperidine N-atom), and which $R^3$ group is substituted at 2-C (relative to the piperidine N-atom) by $S(O)R^{11d}$, $S(O)_2R^{11d}$, alkanoyl, cycloalkanoyl, alkoxy carbonyl, CN, —C(O)—$A^1$—$N(R^{12b})(R^{12c})$, —S(O)—$A^1$—$N(R^{12b})(R^{12c})$, or —$S(O)_2$—$A^1$—$N(R^{12b})(R^{12c})$ wherein $R^{11d}$, $R^{12b}$, $R^{12c}$ and $A^1$ are as hereinbefore defined, may be prepared by reaction of a corresponding compound of formula XX, as hereinbefore defined, with a compound of formula XXIII, $$R^{3a}\text{—}Z \quad \text{XXIII}$$

wherein $R^{3a}$ represents $R^3$ as hereinbefore defined except that it does not represent aryl, and that the $R^{3a}$ chain contains an additional carbon-carbon double bond α,β to the Z-substituent, and Z represents $S(O)R^{11d}$, $S(O)_2R^{11d}$, alkanoyl, cycloalkanoyl, alkoxy carbonyl, CN, —C(O)—$A^1$—$N(R^{12b})(R^{12c})$, —S(O)—$A^1$—$N(R^{12b})(R^{12c})$, or —$S(O)_2$—$A^1$—$N(R^{12b})(R^{12c})$, wherein $R^{11d}$, $R^{12b}$, $R^{12c}$ and $A^1$ are as hereinbefore defined, for example at between room and reflux temperature in the presence of a reaction-inert solvent (e.g. THF).

25. Compounds of formula I in which A represents $C_{2-4}$ alkylene substituted (α to D) with an OH group and D represents $N(R^4)(R^5)$ (at the alkylene chain terminus), and $R^4$ and $R^5$ are as hereinbefore defined, may be prepared by reaction of a compound of formula XXIV,

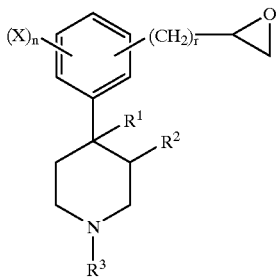

XXIV wherein $R^1$, $R^2$, $R^3$, X, n and r are as hereinbefore defined, with a compound of formula XI, as hereinbefore defined, for example at between room and reflux temperature in the presence of a suitable base (e.g. potassium carbonate) and an appropriate solvent (e.g. N,N-dimethylformamide).

Compounds of formula XXIV may be prepared by dehydration of a corresponding compound of formula I in which A represents a $C_{2-4}$ alkylene substituted (α to D) with an OH group and D represents OH (at the alkylene chain terminus) under conditions well known to those skilled in the art (e.g. by heating in concentrated sulfuric acid).

Compounds of formula XXIV may alternatively be prepared by epoxidation of a corresponding compound of formula I in which A represents a terminal $C_{2-4}$ alkenylene group and D represents H under conditions well known to those skilled in the art (e.g. by reaction with meta-chloroperbenzoic acid).

26. Compounds of formula I in which D represents $N(H)R^4$, wherein $R^4$ is as hereinbefore defined provided that it does not represent aryl, may be prepared by reduction of a corresponding compound of formula XXV,

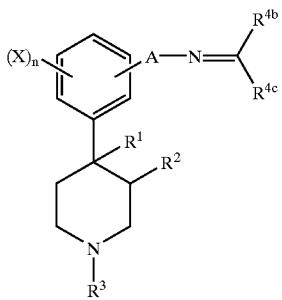

XXV wherein $R^{4b}$ and $R^{4c}$, together with the carbonyl group to which they are attached, form a $C_{1-6}$ alkanal, $C_{3-6}$ alkanone, $C_{3-8}$ cycloalkanone, phenyl($C_{1-4}$)alkanal or phenyl($C_{2-4}$) alkanone group, which five groups are optionally substituted by one or more substituents selected from nitro, halo, $C_{1-4}$ alkyl or $C_{1-4}$ alkoxy (which latter two groups are optionally substituted by one or more halo atoms), and $R^1$, $R^2$, $R^3$, A, X and n are as hereinbefore defined (provided that the —N=C($R^{4b}$)$R^{4c}$ group is not directly attached to an unsaturated carbon atom), for example at between room and reflux temperature in the presence of a mild reducing agent (e.g. sodium borohydride) and a suitable solvent (e.g. a lower alkyl alcohol such as methanol or ethanol).

Compounds of formula XXV may be prepared by reaction of a corresponding compound of formula I in which D represents $NH_2$ with a compound of formula XXVI,

 XXXVI wherein $R^{4b}$ and $R^{4c}$ are as hereinbefore defined, for example at between room and reflux temperature in the presence of a reaction-inert solvent (e.g. a lower alkyl alcohol such as methanol or ethanol) and optionally in the presence of a Lewis-acidic catalyst.

27. Compounds of formula I in which A represents $C_{1-4}$ alkylene, $C_{2-4}$ alkenylene or $C_{2-4}$ alkynylene, which alkylene, alkenylene or alkynylene groups are optionally substituted by one or more substituents selected from $C_{1-4}$ alkyl, $C_{1-4}$ alkoxy, halo or OH, and D represents $N(R^4)(R^5)$ (attached to a $CH_2$ group), wherein $R^4$ and $R^5$ are as hereinbefore defined, may be prepared by reduction of a corresponding compound of formula I in which A represents (as appropriate) a single bond, $C_{1-3}$ alkylene, $C_{2-3}$ alkenylene or $C_{2-3}$ alkynylene, which alkylene, alkenylene or alkynylene groups are optionally substituted by one or more substituents selected from $C_{1-4}$ alkyl, $C_{1-4}$ alkoxy, halo or OH, and D represents $C(O)N(R^4)(R^5)$, for example in the presence of a suitable is reducing agent (e.g. lithium aluminium hydride or a borane derivative) and a reaction-inert solvent (e.g. THF).

Compounds of formulae II, III, VIII, X, $R^{7a}$OH, XI, XII, XIII, XV, XVI, XVIII, XXI, XXII, XXIII, XXVI, and derivatives thereof, when not commercially available or not subsequently described, may be obtained either by analogy with the processes described herein, or by conventional synthetic procedures, in accordance with standard techniques, from readily available starting materials using appropriate reagents and reaction conditions.

Substituents on alkyl, heterocyclic and aryl groups in the above-mentioned compounds may also be introduced, removed and interconverted, using techniques which are well known to those skilled in the art. For example, nitro may be reduced to amino, OH may be alkylated to give alkoxy, alkoxy may be hydrolysed to OH, alkenes may be hydrogenated to alkanes, halo may be hydrogenated to H, etc.

In some cases it is possible to introduce further substituents into the compounds of formula I directly. For example, chlorination of the phenyl group of compounds of formula I, may be performed by reaction with a solution of chlorine in acetic acid.

The skilled person will also appreciate that other various standard substituent or functional group interconversions and transformations within certain compounds of formula I will provide other compounds of formula I.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, OH, amino and carboxylic acid. Suitable protective groups for oxo include acetals, ketals (e.g. ethylene ketals) and dithianes. Suitable protective groups for OH include trialkylsilyl and diarylalkylsilyl groups (e.g. tert-butyldimethylsilyl, tert-butyldiphenylsilyl or trimethylsilyl) and tetrahydropyranyl. Suitable protective groups for amino include tert-butyloxycarbonyl, 9-fluorenylmethoxycarbonyl or benzyloxycarbonyl.

Suitable protective groups for carboxylic acid include $C_{1-6}$ alkyl or benzyl esters. Suitable protective groups for terminal alkynes include trialkylsilyl and diarylalkylsilyl groups (e.g. tert-butyldimethylsilyl, tert-butyldiphenylsilyl or trimethylsilyl).

The protection and deprotection of functional groups may take place before or after any of the reaction steps described hereinbefore.

Protective groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I.

All protected derivatives, and prodrugs, of compounds of formula I are included within the scope of the invention.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

The compounds of the invention are useful because they possess pharmacological activity in animals, especially mammals including humans. They are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the compounds of the invention have been found to be useful in the treatment of diseases mediated via opiate receptors, which diseases include irritable bowel syndrome; constipation; nausea; vomiting; pruritus; and conditions characterised by pruritus as a symptom.

Thus, according to a further aspect of the invention there is provided the use of the compounds of the invention in the manufacture of a medicament for the treatment of a disease mediated via an opiate receptor. There is further provided the use of the compounds of the invention in the manufacture of a medicament for the treatment of irritable bowel syndrome; constipation; nausea; vomiting; pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing a disease mediated via an opiate receptor. There is further provided a method of treating irritable bowel syndrome; constipation; nausea; vomiting; pruritus or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterals, e.g. enrofloxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of diseases mediated via opiate receptors.

The skilled person will also appreciate that compounds of the invention may be taken as a single dose on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test method.

Biological Test

Compounds of the present invention have been found to display activity in binding assays selective for the mu opioid receptor in dog brain. The assays were conducted by the following procedure.

Laboratory bred beagles were used as a source of dog brain tissue. Animals were euthanised, their brains removed and the cerebellum discarded. The remaining brain tissue was sectioned into small pieces approximately 3 g in weight and homogenised in 50 mM Tris pH 7.4 buffer at 4° C. using a Kinematica Polytron™ tissue homogeniser. The resulting homogenate was centrifuged at 48,400× g for 10 minutes and the supernatant discarded. The pellet was resuspended in Tris buffer and incubated at 37° C. for 10 minutes. Centrifugation, resuspension and incubation steps were repeated twice more, and the final pellet was resuspended in Tris buffer and stored at −80° C. Membrane material prepared in this manner could be stored for up to four weeks prior to use.

For mu assays, increasing concentrations of experimental compound, ($5 \times 10^{-12}$ to $10^{-5}$ M), Tris buffer and $^3$H ligand, ([D-Ala$^2$,N-Me-Phe$^4$,Gly-ol$^5$]-Enkephalin, DAMGO), were combined in polystyrene tubes. The reaction was initiated by the addition of tissue, and the mixture was incubated at room temperature for 90 minutes. The reaction was terminated by rapid filtration using a Brandel Cell Harvester™ through Betaplate™ GF/A glass fibre filters pre-soaked in 50 mM Tris pH 7.4, 0.1% polyethylenimine buffer. The filters were then washed three times with 0.5 mL ice-cold Tris pH 7.4 buffer. Washed filters were placed in bags and Starscint™ scintillant added. Bags containing the filters and scintillant were heat sealed and counted by a Betaplate™ 1204 beta counter.

Duplicate samples were run for each experimental compound and the data generated was analysed using IC$_{50}$ analysis software in Graphpad Prism. Ki values were calculated using Graphpad Prism according to the following formula:

$$Ki = IC_{50}/1 + [^3H \text{ ligand}] K_D$$

where IC$_{50}$ is the concentration at which 50% of the $^3$H ligand is displaced by the test compound and K$_D$ is the dissociation constant for the $^3$H ligand at the receptor site.

The invention is illustrated by the following Preparations and Examples in which the following abbreviations may be used:

APCI=atmospheric pressure chemical ionisation
br (in relation to NMR)=broad
DMF=N,N-dimethylformamide
DMSO=dimethylsulfoxide
d (in relation to time)=day
d (in relation to NMR)=doublet
dd (in relation to NMR)=doublet of doublets
EtOAc=ethyl acetate
EtOH=ethanol
h=hour(s)
m (in relation to NMR)=multiplet
MeOH=methanol
min=minute
q (in relation to NMR)=quartet
s (in relation to NMR)=singlet
t (in relation-to NMR)=triplet
THF=tetrahydrofuran When reverse phase HPLC is mentioned in the text the following 2 sets of conditions were employed.

Condition 1: A Phenomenex Magellen™ column, 150×21 mm, packed with 5 m $C_{18}$ silica, eluting with a gradient of acetonitrile: 0.1 M aqueous ammonium acetate (30:70 to 95:5 over 10 mins, flow rate 20 mL per minute).

Condition 2: A Dynamax™ column, 42×250 mm, packed with 8µ $C_{18}$ silica, eluting with acetonitrile : 0.1 M aqueous ammonium acetate (30:70) at 45 mL per minute.

In both cases, combination and evaporation of appropriate fractions, determined by analytical HPLC, provided the desired compounds as acetate salts.

Analytical HPLC conditions used to highlight appropriate fractions were Phenomenex Magellan™ column, 4.6×150 mm, packed with 5µ $C_{18}$ silica, eluting with a gradient of acetonitrile : 0.1 M aqueous heptanesulfonic acid (10:90 to 90:10 over 30 min, followed by a further 10 min at 90:10) at 1 mL per minute. Column oven temperature was 40° C., and ultraviolet detection of components was made at 220 nM.

When column chromatography is referred to this usually refers to a glass column packed with silica gel (40–63 µm). Pressure of ~165 kPa is generally applied and the ratio of crude product: silica gel required for purification is typically 50:1. Alternatively, an Isolute™ SPE (solid phase extraction) column or Waters Sep-Pak™ cartridge packed with silica gel may be used under atmospheric pressure. The ratio of crude product to silica gel required for purification is typically 100:1.

The hydrochloride salt may be made by methods commonly known to those skilled in the art of synthetic chemistry. Typically, to a solution of free base in dichloromethane (1 g :100 mL) was added ethereal hydrochloric acid (1.0 M, 1.2 equivalent), the excess solvent was decanted off and the remaining precipitate was washed three times with ether and then dried in vacuo.

Melting points were determined using a Gallenkamp melting point apparatus and are uncorrected. $^1$H Nuclear magnetic resonance (NMR) spectral data were obtained using a Varian Unity 300 or 400 spectrometer, the observed chemical shifts (δ) being consistent with the proposed structures. Mass spectral (MS) data were obtained on a Fisons Instruments Trio 1000, or a Fisons Instruments Trio 1000 APCI, or a Finnigan Navigator MS, or a Micromass Platform LC spectrometer. The calculated and observed ions quoted refer to the isotopic composition of lowest mass. HPLC means high performance liquid chromatography. Room temperature means 20 to 25° C.

EXAMPLES

Example 1

1-Hexyl-3,4-dimethyl-4-(3-cyanophenyl)piperidine

A solution of 1-hexyl-3,4-dimethyl-4-(3-trifluoromethanesulfonyloxyphenyl)piperidine (Preparation 1, 500 mg, 1.19 mmol) in 1-methyl-2-pyrrolidinone (2.5 mL) was added to a flask containing potassium cyanide (155 mg, 2.38 mmol). The solution was de-oxygenated by evacuating and flushing with nitrogen three times. Catalytic quantities of palladium(II) acetate and 1,1 '-bis (diphenylphosphino)ferrocene were added and the reaction mixture was warmed to 60° C., at which temperature it was stirred for 3 hours. The reaction mixture was cooled to room temperature and poured into saturated aqueous sodium hydrogencarbonate solution (50 mL). The product was extracted into ethyl acetate (3×30 mL). The combined organics were dried ($Na_2SO_4$) and concentrated in vacuo. The residue was purified by column chromatography on silica gel (15 g) eluted with a gradient of ethyl acetate:hexane:0.880 ammonia (20:79:1 to 50:49:1) to give the title compound as an oil (346 mg).

NMR ($CDCl_3$): 0.75 (d, 3H), 0.9 (m, 3H), 1.2–1.4 (m, 9H), 1.4–1.55 (m, 2H), 1.6 (m, 1H), 2.0 (m, 1H), 2.2–2.45 (m, 4H), 2.45–2.65 (m, 2H), 2.8 (m, 1H), 7.35–7.6 (m, 4H).

MS (electrospray): M/Z (MH$^+$) 299.2; $C_{20}H_{30}N_2$+H requires 299.2.

Example 2

1-Hexyl-3,4-dimethyl-4-(3-amidophenyl)piperidine

A mixture of polyphosphoric acid (160 mg) and 1-hexyl-3,4-dimethyl-4-(3-cyanophenyl)piperidine (Example 1, 19 mg, 0.064 mmol) was heated at 115° C. for one hour. The reaction mixture was then cooled to room temperature and diluted with iced water (0.4 mL). Aqueous sodium hydroxide solution (2 N) was added until the pH was 7. The mixture was extracted with ethyl acetate (3×10 mL). The combined organics were dried ($Na_2SO_4$) and the solvent evaporated in vacuo to give a white solid. Purification by column chromatography on silica gel (1 g) eluted with ethyl acetate:ethanol:0.880 ammonia (89:10:1) gave the product as a white solid (6 mg).

NMR ($CDCl_3$, selected data): 0.75 (d, 3H), 0.9 (m, 3H), 1.2–1.4 (m, 9H), 1.4–1.55 (m, 2H), 1.65 (m, 1H), 2.05 (m, 1H), 2.2–2.45 (m, 4H), 2.45–2.6 (m, 2H), 2.8 (m, 1H), 7.35 (t, 1H), 7.45 (d, 1H), 7.55 (d, 1H), 7.8 (s, 1H).

MS (electrospray): M/Z (MH$^+$) 317.3; $C_{20}H_{32}N_2O$+H requires 317.3.

Example 3

1-Hexyl-3,4-dimethyl-4-(3-methoxycarbonylphenyl)-piperidine

To a stirred solution of 1-hexyl-3,4-dimethyl-4-(3-trifluoromethanesulfonyloxyphenyl)piperidine (Preparation 1, 500 mg, 1.19 mmol) in anhydrous N,N-dimethylformamide (6 mL) was added triethylamine (1.7 mL, 12.2 mmol) and anhydrous methanol (1.0 mL, 24.7 mmol). The solution was de-oxygenated by evacuating and flushing with nitrogen five times. Palladium(II) acetate (27 mg, 0.12 mmol) and 1,1 '-bis(diphenylphosphino)ferrocene (67 mg, 0.12 mmol) were added and the mixture was de-oxygenated again, using the same procedure as before. Carbon monoxide gas was bubbled through the mixture for 5 minutes and it was then stirred under an atmosphere of carbon monoxide and heated at 120° C. overnight. The solvent was removed in vacuo to give a brown oil (0.7 g) which was purified by column chromatography on silica gel (35 g) eluted with a gradient of ethyl acetate:hexane:0.880 ammonia (10:190:1 to 10:90:1 to 25:75:1). This gave the title compound as a yellow oil (250 mg).

NMR ($CDCl_3$): 0.75 (d, 3H), 0.9 (m, 3H), 1.2–1.4 (m containing s, 9H), 1.4–1.55 (m, 2H), 1.7 (m, 1H), 2.1 (m, 1H), 2.2–2.45 (m, 4H), 2.45–2.6 (m, 2H), 2.8 (m, 1H), 3.9 (s, 3H), 7.35 (t, 1H), 7.5 (d, 1H), 7.85 (d, 1H), 8.0 (s, 1H).

MS (APCI): M/Z (MH$^+$) 332.4; $C_{21}H_{33}NO_2$+H requires 332.3.

Example 4

1-Hexyl-3,4-dimethyl-4-(3-(N-isopropyl) amidophenyl)-piperidine

In a sealed Wheaton™ vial, 1-hexyl-3,4-dimethyl-4-(3-methoxycarbonylphenyl)piperidine (Example 3, 40 mg, 0.12 mmol) and isopropylamine (5 mL, 59 mmol) were heated together at 150° C. for two days. The reaction mixture was then cooled to room temperature and excess amine was removed by evaporation in vacuo. The residue was purified by column chromatography on silica gel (5 g) eluted with ethyl acetate:ethanol:0.880 ammonia (50:49:1) to give the title compound as an oil (32 mg).

NMR (CDCl$_3$, selected data): 0.75 (d, 3H), 0.9 (m, 3H), 1.2–1.4 (m, 15H), 1.4–1.55 (m, 2H), 1.65 (m, 1H); 2.05 (m, 1H), 2.2–2.45 (m, 4H), 2.45–2.65 (m, 2H), 2.85 (m, 1H), 4.3 (m, 1H) 7.3–7.5 (m, 3H), 7.75 (s, 1H).

MS (electrospray): M/Z (MH$^+$) 359.3; $C_{23}H_{38}N_2O+H$ requires 359.3.

Example 5

1-Hexyl-3,4-dimethyl-4-(3-(N-butyl)amidophenyl)-piperidine

In a sealed Wheaton™ vial, 1-hexyl-3,4-dimethyl-4-(3-methoxycarbonylphenyl)piperidine (Example 3, 30 mg, 0.09 mmol) and n-butylamine (4 mL, 40.5 mmol) were heated together at 140° C. for two days. The reaction mixture was then cooled to room temperature and excess amine was removed by evaporation in vacuo. The residue was purified by column chromatography on silica gel (5 g) eluted with ethyl acetate:hexane:0.880 ammonia (40:49:1) to give the title compound as an oil (20 mg).

NMR (CDCl$_3$, selected data): 0.75 (d, 3H), 0.9 (m, 3H), 0.95 (t, 3H), 1.2–1.8 (m, 16H), 2.05 (m, 1H), 2.2–2.45 (m, 4H), 2.45–2.65 (m, 2H), 2.85 (m, 1H), 3.45 (m, 2H), 7.3–7.55 (m, 3H), 7.75 (s, 1H).

MS (electrospray): M/Z (MH$^+$) 373.3; $C_{24}H_{40}N_2O+H$ requires 373.3.

Example 6

1-Hexyl-3,4-dimethyl-4-(3-(N-propyl)amidophenyl)-piperidine

In a sealed Wheaton™ vial, 1-hexyl-3,4-dimethyl-4-(3-methoxycarbonylphenyl)piperidine (Example 3, 30 mg, 0.09 mmol) and n-propylamine (4 mL, 94 mmol) were heated together at 140° C. for two days. The reaction mixture was then cooled to room temperature and excess amine was removed by evaporation in vacuo. The residue was purified by column chromatography on silica gel (5 g) eluted with ethyl acetate: ethanol: 0.880 ammonia (50:49:1) to give the title compound as an oil (3.5 mg).

NMR (CDCl$_3$, selected data): 0.75 (d, 3H), 0.9 (m, 3H), 1.0 (t, 3H), 1.25–1.4 (m, 9H), 1.4–1.55 (m, 2H), 1.6–1.75 (m, 3H), 2.05 (m, 1H), 2.2–2.45 (m, 4H), 2.45–2.65 (m, 2H), 2.8 (m, 1H), 3.45 (m, 2H), 7.3–7.5 (m, 3H), 7.75 (s, 1H).

MS (electrospray): M/Z (MH$^+$) 359.3; $C_{23}H_{38}N_2O+H$ requires 359.3.

Example 7

1-Hexyl-3,4-dimethyl-4-(3-(N-benzyl) amidophenyl)-piperidine

In a sealed Wheaton™ vial, 1-hexyl-3,4-dimethyl-4-(3-methoxycarbonylphenyl)piperidine (Example 3, 30 mg, 0.09 mmol) and benzylamine (3 mL, 27.5 mmol) were heated together at 100° C. for 76 hours. The reaction mixture was cooled to room temperature, concentrated and the residue purified by column chromatography on silica gel eluted with a gradient of hexane:ethyl acetate (20:80 to 50:50). The title compound was obtained as a pale oil (13 mg).

NMR (CDCl$_3$, selected data): 0.75 (d, 3H), 0.9 (t, 3H), 1.2–1.4 (m, 9H), 1.6–1.55 (m, 2H), 1.65 (m, 1H), 2.05 (m, 1H), 2.2–2.45 (m, 4H), 2.45–2.65 (m, 2H), 2.85 (m, 1H), 4.65 (m, 2H), 7.3–7.4 (m, 6H), 7.45 (d, 1H), 7.55 (d, 1H), 7.8 (s, 1H). MS (electrospray): M/Z (MH$^+$) 407.3; $C_{27}H_{38}N_2O+H$ requires 407.3.

Example 8

1-Hexyl-3,4-dimethyl-4-(3-(N-ethyl)amidophenyl)-piperidine

In a sealed Wheaton™ vial, 1-hexyl-3,4-dimethyl-4-(3-methoxycarbonyl-phenyl)piperidine (Example 3, 30 mg, 0.09 mmol) and ethylamine (3 mL, 45.8 mmol) were heated together at 1 00C for 60 hours. The ethylamine was found to be evaporating, thus the reaction mixture was transferred to a sealed bomb and heated at 100° C. and 690 kPa for a further 16 hours. The reaction mixture was cooled to room temperature, concentrated and then purified by column chromatography on silica gel eluted with a gradient of hexane-:ethyl acetate (20:80 to 50:50). The title compound was obtained as a pale oil (11 mg).

NMR (CDCl$_3$, selected data): 0.75 (d, 3H), 0.9 (m, 3H), 1.2–1.4 (m, 12H), 1.4–1.55 (m, 2H), 1.65 (m, 1H), 2.05 (m, 1H), 2.2–2.45 (m, 4H), 2.45–2.65 (m, 21), 2.85 (m, 1H), 3.5 (m, 2H), 7.35 (t, 1H), 7.4 (d, 1H), 7.5 (d, 1H), 7.75 (s, 1H).

MS (thermospray): M/Z (MH$^+$) 345.1 $C_{22}H_{36}N_2O+H$ requires 345.3.

Example 9

1-Hexyl-3,4-dimethyl-4-(3-(N-isobutyl) amidophenyl)-piperidine

The title compound was prepared by the method of Example 7, substituting benzylamine with isobutylamine (3 mL, 30.18 mmol). This gave the title compound as a pale oil (9 mg).

NMR (CDCl$_3$, selected data): 0.75 (d, 3H), 0.9 (t, 3H), 1.0 (d, 6H), 1.2–1.35 (m, 9H), 1.4–1.55 (m, 2H), 1.65 (m, 1H), 1.9 (m, 1H), 2.05 (m, 1H), 2.2–2.45 (m, 4H), 2.45–2.65 (m, 2H), 2.8 (m, 1H), 3.3, (t, 2H), 7.35 (t, 1H), 7.45 (d, 1H), 7.5 (d, 1H), 7.75 (s, 1H).

MS (electrospray): M/Z (MH$^+$) 373.3; $C_{24}H_{40}N_2O+H$ requires 373.3.

Example 10

1-Hexyl-3,4-dimethyl-4-{3-[N-(2-methoxyethyl)]-amidophenyl}piperidine

In a sealed Wheaton™ vial, 1-hexyl-3,4-dimethyl-4-(3-methoxycarbonyl-phenyl)piperidine (Example 3, 30 mg, 0.09 mmol) and 2-methoxyethylamine (3 mL, 34.5 mmol) were heated together at 130° C. for 120 hours. The reaction mixture was cooled to room temperature, concentrated and purified by column chromatography on silica gel eluted with a gradient of hexane:ethyl acetate:0.880 ammonia gradient (10:89:1 to 49:50:1). The gave the title compound as a pale oil (8 mg).

NMR (CDCl$_3$, selected data): 0.75 (d, 3H), 0.9 (m, 3H), 1.2–1.4 (m, 9H), 1.4–1.55 (m, 2H), 1.65 (m, 1H), 2.05 (m, 1H), 2.2–2.45 (m, 4H), 2.45–2.65 (m, 2H), 2.8 (m, 1H), 3.3–3.7 (m, 7H), 7.35 (t, 1H), 7.4 (d, 1H), 7.5 (d, 1H), 7.75 (s, 1H).

MS (APCI): M/Z (MH$^+$) 374.5; $C_{23}H_{38}N_2O_2+H$ requires 374.3.

Example 11

1-Hexyl-3,4-dimethyl-4-(3-(N-methyl)amidophenyl)-piperidine

To a suspension of anhydrous methylamine hydrochloride (17 mg, 0.25 mmol) in anhydrous toluene (0.5 mL) stirred under nitrogen and cooled in an ice bath was added a solution of trimethylaluminium (2.0 M in toluene, 0.12 mL, 0.24 mmol). The mixture was allowed to warm to room temperature while stirring for 4 hours, then it was treated with a solution of 1-hexyl-3,4-dimethyl-4-(3-methoxycarbonylphenyl)piperidine (Example 3, 40 mg, 0.12 mmol) in anhydrous toluene (1.5 mL). The resulting mixture was heated at reflux overnight, then quenched with dilute hydrochloric acid (10 mL of 2 N) and extracted with diethyl ether (10 mL). The aqueous phase was basified to pH 13 with aqueous sodium hydroxide solution (2 N) and extracted with dichloromethane (3×20 mL). The combined dichloromethane extracts were dried ($Na_2SO_4$) and concentrated in vacuo to give an orange oil (31 mg) which was purified by column chromatography on silica gel (1.2 g) eluted with ethyl acetate:hexane:0.880 ammonia (50:50:1). This gave the title compound as a colourless residue (17 mg).

NMR ($CDCl_3$, selected data): 0.75 (d, 3H), 0.9 (m, 3H), 1.2–1.4 (m, 9H), 1.4–1.55 (m, 21), 1.65 (m, 1H), 2.05 (m, 1H), 2.2–2.45 (m, 4H), 2.45–2.65 (m, 2H), 2.8 (m, 1H), 3.0 (d, 3H), 7.35 (t, 1H), 7.4 (d, 1H), 7.5 (d, 1H), 7.75 (s, 1H).

MS (APCI) M/Z (MH$^+$) 331.1; $C_{21}H_{34}N_2O$+H requires 331.3.

Example 12

1-Hexyl-3,4-dimethyl-4-(3-(N,N-dimethyl)amidophenyl)-piperidine

The title compound was prepared as for Example 11 except using anhydrous dimethylamine hydrochloride (20 mg, 0.25 mmol) in place of methylamine hydrochloride. This gave a pale yellow oil (38 mg).

NMR ($CDCl_3$): 0.75 (d, 3H), 0.9 (m, 3H), 1.2–1.4 (m, 9H), 1.4–1.55 (m, 2H), 1.65 (m, 1H), 2.0 (m, 1H), 2.2–2.45 (m, 4H), 2.45–2.65 (m, 2H), 2.8 (m, 1H), 2.95 (br s, 3H), 3.1 (br s, 3H), 7.15–7.25 (m, 1H), 7.25–7.4 (m, 3H).

MS (thermospray): M/Z (MH$^+$) 345.2; $C_{22}H_{36}N_2O$+H requires 345.3.

Example 13

1-Hexyl-3,4-dimethyl-4-(3-(N,N-diethyl)amidophenyl)-piperidine

To a suspension of anhydrous diethylamine hydrochloride (30 mg, 0.27 mmol) in anhydrous toluene (0.5 mL) stirred under nitrogen and cooled in an ice bath was added a solution of trimethylaluminium (2.0 M in toluene, 0.14 mL, 0.28 mmol). The mixture was allowed to warm to room temperature while stirring for 2 hours, then it was treated with a solution of 1-hexyl-3,4-dimethyl-4-(3-methoxycarbonylphenyl)piperidine (Example 3, 44 mg, 0.13 mmol) in anhydrous toluene (1 mL). The resulting mixture was heated at reflux for 2½ days, then quenched with dilute hydrochloric acid (10 mL of 2 N) and extracted with diethyl ether (10 mL). The aqueous phase was basified to pH 13 with aqueous sodium hydroxide solution (2 N) and extracted with dichloromethane (3×20 mL). The combined dichloromethane extracts were dried ($Na_2SO_4$) and concentrated in vacuo to give an orange oil (52 mg) which was purified by column chromatography on silica gel (1.5 g) eluted with a gradient of ethyl acetate:hexane:0.880 ammonia (10:90:1 to 20:40:1). This gave the title compound as a yellow oil (34 mg).

NMR ($CDCl_3$): 0.75 (d, 3H), 0.9 (m, 3H), 1.0–1.4 (m, 15H), 1.4–1.55 (m, 2H), 1.65 (m, 1H), 2.0 (m, 1H), 2.2–2.45 (m, 4H), 2.45–2.65 (m, 2H), 2.8 (m, 1H), 3.25 (br m, 2H), 3.55 (br m, 2H), 7.1–7.2 (m, 1H), 7.2–7.35 (m, 3H).

MS (APCI): M/Z (MH$^+$) 373.1; $C_{24}H_{40}N_2O$+H requires 373.3.

Example 14

1-Hexyl-3,4-dimethyl-4-(3-(N-tert-butyl)amidophenyl)-piperidine

A solution of 1-hexyl-3,4-dimethyl-4-(3-methoxycarbonylphenyl)-piperidine (Example 3, 40 mg, 0.12 mmol) in dilute hydrochloric acid (5 mL of 2 N) was heated at reflux overnight. The solvent was removed in vacuo and the residue was taken up in methanol and re-concentrated in vacuo to give a brown oil (40 mg) which was dissolved in dichloromethane (1 mL) and treated with 1-(3-dimethylaminopropyl)-3-ethylcarbodiimide hydrochloride (25 mg, 0.13 mmol), N-methylmorpholine (27 µL; 0.25 mmol) and tert-butylamine (14 µL, 0.13 mmol). The resulting mixture was stirred at room temperature overnight, then poured into saturated aqueous sodium hydrogencarbonate solution (5 mL.) and extracted with dichloromethane (3×5 mL). The combined extracts were dried ($Na_2SO_4$) and concentrated in vacuo to give a brown residue which was purified by column chromatography on silica gel (2.5 g) eluted with a gradient of ethyl acetate:hexane:0.880 ammonia (5:95:1 to 10:90:1 to 20:80:1 to 30:70:1). This gave the title compound as a colourless residue (10 mg).

NMR ($CDCl_3$, selected data): 0.75 (d, 3H), 0.9 (m, 3H), 1.2–1.4 (m, 9H), 1.4–1.55 (m, 1H), 1.65 (m, 1H), 2.05 (m, 1H), 2.2–2.45 (m, 4H), 2.45–2.6 (m, 2H), 2.8 (m, 1H), 7.3–7.45 (m, 3H), 7.75 (s, 1H).

MS (APCI): M/Z (MH$^+$) 373.1; $C_{24}H_{40}N_2O$+H requires 373.3.

Example 15

1-Benzyl-3,4-dimethyl-4-(3-methoxycarbonylphenyl)-piperidine

A stirred solution of 1-benzyl-3,4-dimethyl-4-(3-trifluoromethanesulfonyloxyphenyl)piperidine (Preparation 2, 506 mg, 1.18 mmol), triethylamine (1.6 mL, 11.8 mmol) and anhydrous methanol (1.9 mL, 46.8 mmol) in anhydrous N,N-dimethylformamide (6 mL) was de-oxygenated by evacuating and flushing with nitrogen five times. Palladium (II) acetate (30 mg, 0.13 mmol) and 1,1'-bis(diphenylphosphino)ferrocene (63 mg, 0.11 mmol) were added and the mixture was again de-oxygenated, using the same method as before. Carbon monoxide gas was bubbled through the mixture for ca 5 minutes and it was subsequently heated at 80° C. under an atmosphere of carbon monoxide overnight. The mixture was then poured into water (100 mL) and extracted with diethyl ether (3×100 mL). The combined extracts were dried ($Na_2SO_4$) and concentrated in vacuo to give an orange oil (250 mg). A black residue remaining in the reaction flask, insoluble in diethyl ether, was dissolved in dichloromethane and transferred to the separating funnel containing the aqueous layer and this was re-extracted with dichloromethane (3×50 mL). The combined organics were filtered through Celite® to remove residual palladium, dried (Na$_2$SO$_4$) and concentrated in vacuo to give a brown oil (270 mg). The combined oils were purified by silica (25 g) column chromatography eluting with a gradient of hexane-:ethyl acetate:0.880 ammonia (140:10:1 to 90:10:1) to give the title compound as a colourless oil (335 mg).

NMR (CDCl$_3$): 0.75 (d, 3H), 1.35 (s, 3H), 1.65 (m, 1H), 2.05 (m, 1H), 2.3–2.5 (m, 2H), 2.5–2.65 (m, 2H), 2.85 (m, 1H), 3.45 (d, 1H), 3.6 (d, 1H), 3.9 (s, 3H), 7.2–7.4 (m, 6H), 7.5 (d, 1H), 7.85 (d, 1H), 8.0 (s, 1

MS (thermospray): M/Z (MH$^+$) 338.2; C$_{22}$H$_{27}$NO$_2$+H requires 338.2.

Example 16

1-Benzyl-3,4-dimethyl-4-(3-(N-ethyl)amidophenyl)-piperidine

A stirred suspension of ethylamine hydrochloride (880 mg, 10.8 mmol) in anhydrous toluene (10 mL) was de-oxygenated by evacuating and flushing with nitrogen three times. Stirring under nitrogen it was cooled in an ice bath and treated with trimethylaluminium solution (2.0 M in toluene, 5.4 mL, 10.8 mmol) via syringe. The mixture was allowed to warm to room temperature while stirring for 1¼ hours. A solution of 1-benzyl-3,4-dimethyl-4-(3-methoxycarbonylphenyl)piperidine (Example 15, 1.81 g, 5.36 mmol) in anhydrous toluene (20 mL) was added via syringe and the reaction mixture was heated at reflux overnight. After it had cooled, aqueous hydrochloric acid (100 mL of 2 N) was added and the mixture was extracted with diethyl ether (100 mL). The organic extract was back-washed with aqueous hydrochloric acid (50 mL of 2 N). The combined aqueous phases were basified to pH 13 with aqueous sodium hydroxide solution (2 it and then extracted with dichloromethane (300 mL followed by 2×100 mL). The combined dichloromethane extracts were washed with water (150 mL) followed by saturated aqueous sodium chloride solution (150 mL), dried (Na$_2$SO$_4$) and concentrated in vacuo to give a brown oil (2.0 g). Purification by silica (100 g) column chromatography eluting with a gradient of ethyl acetate:hexane:0.880 ammonia (20:80:1 to 30:70:1 to 40:60:1) gave the title compound as a cream foam (805 mg).

NMR (CDCl$_3$, selected data): 0.75 (d, 3H), 1.25 (t, 3H), 1.35 (s, 3H), 1.65 (m, 1H), 2.05 (m, 1H), 2.35–2.45 (m, 2H), 2.5–2.6 (m, 2H), 2.85 (m, 1H), 3.4–3.55 (m, 3H), 3.6 (d, 1H), 7.2–7.35 (m, 6H), 7.4 (d, 1H), 7.5 (d, 1H), 7.75 (s, 1H).

MS (APCI): M/Z (MH$^+$) 351.3; C$_{23}$H$_{30}$N$_2$O+H requires 351.2.

Example 17

1-(2-Phenoxyethyl)-3,4-dimethyl-4-(3-(N-ethyl)-amidophenyl)piperidine

A stirred mixture of 3,4-dimethyl-4-(3-(N-ethyl) amidophenyl)piperidine (Preparation 3, 50 mg, 0.19 mmol), 2-bromoethyl phenyl ether (42 mg, 0.20 mmol), and sodium hydrogencarbonate (19.1 mg, 0.22 mmol) in anhydrous N,N-dimethylformamide (1 mL) was heated at 100° C. for 2 hours. The solvent was then removed in vacuo to give a brown oil which was purified by column chromatography on silica gel (4 g) eluted initially with CH$_2$Cl$_2$, changing incrementally to CH$_2$Cl$_2$:MeOH (25:1), to give the title compound as a yellow oil (55 mg).

NMR (CDCl$_3$, selected data): 0.75 (d, 3H), 1.25 (t, 3H), 1.35 (s, 3H), 1.65 (m, 1H), 2.05 (m, 1H), 2.35 (m, 1H), 2.55 (m, 1H), 2.6–2.8 (m, 3H), 2.8–2.95 (m, 2H), 3.5 (m, 2H), 4.1 (m, 2H), 6.9–7.0 (m, 3H), 7.3 (m, 2H), 7.35 (m, 1H), 7.4 (m, 1H), 7.5 (d, 1H), 7.75 (s, 1H).

MS (thermospray): M/Z (MH$^+$) 381.2; C$_{24}$H$_{32}$N$_2$O$_2$+H requires 381.3.

Example 18

1-(5-Methylhexyl)-3,4-dimethyl-4-(3-(N-ethyl)-amidophenyl)piperidine

A stirred mixture of 3,4-dimethyl-4-(3-(N-ethyl) amidophenyl)piperidine (Preparation 3, 50 mg, 0.19 mmol), 1-bromo-5-methylhexane (37 mg, 0.20 mmol), and sodium hydrogencarbonate (19.1 mg, 0.22 mmol) in anhydrous N,N-dimethylformamide (1 mL) was heated at 100° C. for 2½ hours. The solvent was then removed in vacuo to give a brown oil which was purified by column chromatography on silica gel (4 g) eluted initially with CH$_2$Cl$_2$, changing incrementally to CH$_2$Cl$_2$:MeOH (25:1), to give the title compound as a yellow oil (58 mg).

NMR (CDCl$_3$, selected data): 0.75 (d, 3H), 0.85 (d, 6H), 1.15 (m, 2H), 1.2–1.35 (m, 8H), 1.35–1.6 (m, 3H), 1.65 (m, 1H), 2.05 (m, 11H), 2.2–2.45 (m, 4H), 2.45–2.65 (m, 2H), 2.85 (m, 1H), 3.5 (m, 2H), 7.35 (t, 1H), 7.4 (d, 1H), 7.5 (d, 1H), 7.75 (s, 1H).

MS (thermospray): M/Z (MH$^+$) 359.5; C$_{23}$H$_{38}$N$_2$O+H requires 359.3.

Example 19

1-(3-Phenylpropyl)-3,4-dimethyl-4-(3-(N-ethyl)-amidophenyl)piperidine

A stirred mixture of 3,4-dimethyl-4-(3-(N-ethyl) amidophenyl)piperidine (Preparation 3, 50 mg, 0.19 mmol), 1-bromo-3-phenylpropane (32 µL, 0.21 mmol), and sodium hydrogencarbonate (19.1 mg, 0.22 mmol) in anhydrous N,N-dimethylformamide (1 mL) was heated at 100° C. for 2 hours. The solvent was then removed in vacuo to give a brown oil which was purified by column chromatography on silica gel (4 g) eluted initially with CH$_2$Cl$_2$, changing incrementally to CH$_2$Cl$_2$:MeOH (25:1), followed by further purification by column chromatography on silica gel (4 g) eluted with a gradient of CH$_2$Cl$_2$ MeOH (50:1 to 50:2). This gave the title compound as a yellow oil (55 mg).

NMR (CDCl$_3$, selected, data): 0.75 (d, 3H), 1.25 (t, 3H), 1.3 (s, 3H), 1.65 (m, 1H), 1.8 (m, 2H), 2.05 (m, 1H), 2.25–2.45 (m, 4H), 2.45–2.7 (m, 4H), 2.85 (m, 1H), 3.5 (m, 2H), 7.15–7.2 (m, 3H), 7.25 (m, 2H), 7.35 (t, 1H), 7.4 (d, 1H), 7.5 (d, 11), 7.75 (s, 1H).

MS (thermospray): M/Z (MH$^+$) 379.0; C$_{25}$H$_{34}$N$_2$O+H requires 379.3.

Example 20

1-(5-Cyanopentyl)-3,4-dimethyl-4-(3-(N-ethyl)-amidophenyl)piperidine

A stirred mixture of 3,4-dimethyl-4-(3-(N-ethyl) amidophenyl)piperidine (Preparation 3, 50 mg, 0.19 mmol), 6-bromohexanenitrile (28 µL, 0.20 mmol), and sodium hydrogencarbonate (19.1 mg, 0.22 mmol) in anhydrous N,N-dimethylformamide (1 mL) was heated at 100° C. for 4 hours. The solvent was then removed in vacuo to give a brown oil which was purified by column chromatography on silica gel (4 g) eluted initially with CH$_2$Cl$_2$, changing incrementally to CH$_2$Cl$_2$:MeOH (25:1), to give a yellow oil (82 mg), followed by further purification by column chromatography on silica gel (4 g) eluted with a gradient of CH$_2$Cl$_2$:MeOH (50:1 to 50:2). This gave the title compound as a yellow oil (54 mg).

NMR (CDCl$_3$, selected data): 0.8 (d, 3H), 1.25 (t, 3H), 1.35 (s, 3H), 1.5 (m, 2H), 1.55–1.8 (m, 5H), 2.15 (m, 1H), 2.35 (t, 2H), 2.4–2.6 (m, 4H), 2.6–2.75 (m, 2H), 2.95 (m, 1H), 3.5 (m, 2H), 7.3–7.45 (m, 2H), 7.5 (d, 1H), 7.75 (s, 1H).

MS (thermospray): M/Z (MH$^+$) 356.4; C$_{22}$H$_{33}$N$_3$O+H requires 356.3.

Example 21

1-Hexyl-3,4-dimethyl-4-(3-aminomethylphenyl) piperidine

To a stirred solution of 1-hexyl-3,4-dimethyl-4-(3-cyanophenyl)piperidine (Example 1, 800 mg, 2.68 mmol) in anhydrous tetrahydrofuran (40 mL) at 0° C. under nitrogen was added lithium aluminium hydride (1.0 M in tetrahydrofuran, 4.0 mL, 4.0 mmol). The reaction mixture was allowed to warm to room temperature, before being heated to 37° C. for 30 minutes. Subsequently, diethyl ether (50 mL), then aqueous sodium hydroxide (0.3 mL, 15% w/v solution) and finally water (0.45 mL) were added. The white solid formed was filtered off. The filtrate was washed with saturated aqueous sodium hydrogencarbonate solution (2×50 mL). The aqueous phases were back-extracted with diethyl ether (50 mL). The combined organics were dried (MgSO$_4$) and concentrated in vacuo to give the title compound as an oil (770 mg).

NMR (CDCl$_3$, selected data): 0.75 (d, 3H), 0.9 (m, 3H), 1.2–1.4 (m, 9H), 1.4–1.55 (m, 2H), 1.65 (m, 1H), 2.0 (m, 1H), 2.2–2.45 (m, 4H), 2.45–2.6 (m, 2H), 2.8 (m, 1H), 3.85 (s, 2H), 7.1–7.35 (m, 4H).

MS (APCI): M/Z (MH$^+$) 303.4; C$_{20}$H$_{34}$N$_2$+H requires 303.3.

Example 22

1-Hexyl-3,4-dimethyl-4-(3-(N-methoxycarbonyl) aminomethylphenyl)piperidine

To a stirred solution of 1-hexyl-3,4-dimethyl-4-(3-aminomethylphenyl)-piperidine (Example 21, 100 mg, 0.33 mmol) in pyridine (2 mL, dried over basic alumina) at 0° C. under nitrogen was added methyl chloroformate (40 µL, 0.52 mmol). The reaction mixture was stirred at room temperature under a nitrogen atmosphere overnight. Subsequently, ice was added followed by aqueous sodium hydroxide (5 N solution) to give a pH of 11. The mixture was extracted with diethyl ether (3×25 mL). The combined organic phases was dried (MgSO$_4$) and then concentrated in vacuo at 70° C. to give an oil (104 mg) which was purified by column chromatography on silica gel (2.9 g) eluted with a gradient of ethyl acetate:hexane (1:2 to 2:1). This gave the title compound as an oil (65 mg).

NMR (CDCl$_3$, selected data): 0.75 (d, 3H), 0.9 (m, 3H), 1.2–1.35 (m, 9H), 1.4–1.55 (n, 2H), 1.6 (n, 1H), 2.0 (m, 1H), 2.2–2.4 (n, 4H), 2.4–2.6 (m, 2H), 2.8 (n, 1H), 3.7 (s, 3H), 4.35 (d, 2H), 7.1 (d, 1H), 7.15–7.35 (m, 3H).

MS (thermospray): M/Z (MH$^+$) 361.4; C$_{22}$H$_{36}$N$_2$O$_2$+H requires 361.3.

Example 23

1-Hexyl-3,4-dimethyl-4-(3-(N-acetyl) aminomethylphenyl)-piperidine

This preparation was carried out using the procedure described for Example 22 except using acetyl chloride (35 µL, 0.49 mmol) in place of methyl chloroformate. This gave the title compound as an oil (100 mg).

NMR (CDCl$_3$, selected data): 0.75 (d, 3H), 0.9 (m, 3H), 1.2–1.4 (m, 9H), 1.4–1.55 (m, 2H), 1.6 (m, 1H), 1.95–2.05 (m, 4H), 2.2–2.4 (m, 4H), 2.4–2.6 (m, 2H), 2.8 (m, 1H), 4.4 (d, 2H), 7.1 (d, 1H), 7.15–7.35 (m, 3H).

MS (APCI): M/Z (MH$^+$) 345.3; C$_{22}$H$_{36}$N$_2$O+H requires 345.3.

Example 24

1-Hexyl-3,4-dimethyl-4-(3-(N-methanesulfonyl) aminomethylphenyl)piperidine

This preparation was carried out using the procedure described for Example 22 except using methanesulfonyl chloride (40 µL, 0.52 mmol) in place of methyl chloroformate. This gave the title compound as an oil (94mg).

NMR (CDCl$_3$, selected data): 0.75 (d, 3H), 0.9 (m, 3H), 1.2–1.4 (m, 9H), 1.4–1.55 (m, 2H), 1.6 (m, 1H), 2.0 (m, 1H), 2.2–2.4 (m, 4H), 2.4–2.65 (m, 2H), 2.75–2.9 (m, 4H), 4.3 (s, 2H), 7.15 (d, 1H), 7.2–7.35 (m, 3H).

MS (APCI): M/Z (MH$^+$) 381.6; C$_{21}$H$_{36}$N$_2$O$_2$S+H requires 381.3.

Example 25

1-Hexyl-3,4-dimethyl-4-(3-(N-trifluoromethanesulfonyl)-aminomethylphenyl) piperidine To a solution of 1-hexyl-3,4-dimethyl-4-(3-aminomethylphenyl)piperidine (Example 21, 100 mg, 0.33 mmol) in pyridine (1.5 mL, dried over basic alumina) stirred under nitrogen was added trifluoromethanesulfonyl chloride (0.3 mL, 0.28 mmol). The reaction mixture was stirred at room temperature under a nitrogen atmosphere overnight. Aqueous sodium hydroxide (20 mL of 2) was added and the mixture was extracted with dichloromethane (3×20 mL). The aqueous layer was treated with dilute aqueous hydrochloric acid (20 mL of 1 N) and then extracted with dichloromethane (2×20 mL). The organic phases were combined, dried (MgSO$_4$) and concentrated in vacuo to give an orange oil (40 mg) which was purified by column chromatography on silica gel (1.2 g) eluted with a gradient of ethyl acetate:hexane:triethylamine (20:80: 1) to ethyl acetate:triethylamine (100:1). This gave the title compound as an oil (30 mg).

NMR (CDCl$_3$, selected data): 0.75 (d, 3H), 0.9 (m, 3H), 1.2–1.4 (m, 9H), 1.4–1.55 (m, 2H), 1.65 (m, 1H), 2.05 (m, 1H), 2.2–2.75 (m, 6H), 2.8 (m, 1H), 4.4 (s, 2H), 7.15 (d, 1H), 7.2–7.35 (m, 3H).

MS (thermospray): M/Z (MH$^+$) 435.1; C$_{21}$H$_{33}$F$_3$N$_2$O$_2$S+H requires 435.2.

Example 26

1-Hexyl-3,4-dimethyl-4-(3-vinylphenyl)piperidine

A solution of 1-hexyl-3,4-dimethyl-4-(3-trifluoromethanesulfonyloxyphenyl)piperidine (Preparation 1, 1.5 g, 3.6 mmol) in 1,4-dioxan (17 mL) was de-oxygenated by evacuating and flushing with nitrogen five times. Vinyl tributyl tin (1.06 mL, 3.71 mmol) was added under stirring, followed by lithium chloride (456 mg, 10.76 mmol), tetrakis(triphenylphosphine)palladium(0) (catalytic) and 2,6-di-tert-butyl-4-methylphenol (2 crystals). The suspension was stirred under nitrogen and heated at reflux for ten hours. After cooling to room temperature the reaction mixture was quenched with aqueous ammonium hydroxide solution (50 mL, 1.0 M) and further diluted with ethyl acetate (50 mL). The phases were separated and the aqueous layer was further extracted with ethyl acetate (3×25 mL). The combined organics were dried (Na$_2$SO$_4$) and concentrated in vacuo. The residual oil was purified by column chromatography on silica gel (120 g) eluted with ethyl acetate:hexane:0.880 ammonia (39:60:1) to give the title compound as an oil (890 mg).

NMR (CDCl$_3$): 0.75 (d, 3H), 0.85 (m, 3H), 1.2–1.4 (m, 9H), 1.4–1.55 (m, 2H), 1.65 (m, 1H), 2.05 (m, 1H), 2.2–2.45 (m, 4H), 2.45–2.65 (m, 2H), 2.85 (m, 1H), 5.25 (d, 1H), 5.75 (d, 1H), 6.7 (dd, 1H), 7.1–7.35 (m, 4H).

MS (thermospray): M/Z (MH$^+$) 300.4; C$_{21}$H$_{33}$N+H requires 300.3.

Example 27

1-Hexyl-3,4-dimethyl-4-(3-(1,2-dihydroxyethyl) phenyl)-piperidine

1-Hexyl-3,4-dimethyl-4-(3-vinylphenyl)piperidine (Example 26, 200 mg, 0.67 mmol) was dissolved in a mixture of water (2 mL) and acetone (18 mL). 4-methylmorpholine N-oxide (172 mg, 1.47 mmol) was added with stirring followed by osmium tetroxide (200 μL, 2.5% w/w in tert-butanol). The reaction mixture was stirred at room temperature for 4 hours before the solvent was removed by evaporation in vacuo. The residue was partitioned between dichloromethane (25 mL) and water (25 mL). The organic phase was separated and dried (Na$_2$SO$_4$). Concentration in vacuo gave a residue which was purified by column chromatography on silica gel (10 g) eluted with a gradient of ethyl acetate:hexane:ammonium hydroxide solution (50:49:1 to 60:33:1), followed by ethyl acetate:methanol:ammonium hydroxide solution (94:5:1). Combination of the appropriate fractions and evaporation to dryness in vacuo gave the product as a yellow oil (145 mg).

NMR (CDCl$_3$, selected data): 0.75 (d, 3H), 0.9 (n, 3H), 1.2–1.4 (m, 9H), 1.4–1.55 (m, 2H), 1.6 (m, 1H), 2.05 (n, 1H), 2.2–2.45 (n, 4H), 2.45–2.65 (n, 2H), 2.8 (m, 1H), 3.7 (m, 2H), 4.80 (n, 1H), 7.1–7.4 (m, 4H).

MS (thermospray): M/Z (MH$^+$) 334.5; C$_{21}$H$_{35}$NO$_2$+H requires 334.3.

Example 28

1-Hexyl-3,4-dimethyl-4-(3-formylphenyl)piperidine

1-Hexyl-3,4-dimethyl-4-(3-vinylphenyl)piperidine (Example 26, 200 mg, 0.67 mmol) was dissolved in a mixture of water (2 μL) and acetone (18 mL). Osmium tetroxide (200 μL, 2.5% w/w in tert-butanol) was added, followed by sodium periodate (572 mg, 2.68 mmol) which was added portionwise. The reaction mixture was stirred at room temperature for 26 hours, then it was filtered to remove precipitate and the solvent was removed by evaporation in vacuo. The residue was partitioned between dichloromethane (25 mL) and saturated sodium chloride solution (25 mL). The organic phase was separated, dried (Na$_2$SO$_4$) and the solvent removed in vacuo. The residue was purified by column chromatography on silica gel (50 g) eluted with ethyl acetate:hexane:0.880 ammonia (74:25:1). The title compound was obtained as an oil (80 mg).

NMR (CDCl$_3$): 0.75 (d, 3H), 0.9 (m, 3H), 1.2–1.4 (m, 9H), 1.4–1.6 (m, 2H), 1.65 (m, 1H), 2.05 (m, 1H), 2.2–2.45 (m, 4H), 2.45–2.65 (m, 2l1), 2.85 (m, 11H), 7.5 (t, 1H), 7.55 (d, 1H), 7.7 (d, 1H), 7.8 (s, 1H), 10.0 (s, 1H).

MS (electrospray): M/Z (MH$^+$) 302.0; C$_{20}$H$_{31}$NO+H requires 302.2.

Example 29

1-Hexyl-3,4-dimethyl-4-(3-(N-hydroxy) iminomethylphenyl)piperidine

A solution of 1-hexyl-3,4-dimethyl-4-(3-formylphenyl) piperidine (Example 28, 80 mg, 0.27 mmol) in a mixture of pyridine (1 mL) and ethanol (1 mL) was treated with hydroxylamine hydrochloride (22 mg, 0.32 mmol) and the resulting mixture was heated at reflux for 18 hours. The solvent was evaporated in vacuo and the residual orange oil was purified by column chromatography on silica gel (10 g) eluted with a gradient of dichloromethane:methanol:0.880 ammonia (98:1:1 to 94:5:1). This gave the title compound as an oil (18 mg).

NMR (CDCl$_3$, selected data): 0.8 (d, 3H), 0.85 (m, 3H), 1.2–1.4 (m, 9H), 1.4–1.6 (m, 2H), 1.7 (m, 1H), 2.1 (m, 1H), 2.2–2.75 (m, 6H), 2.95 (m, 1H), 7.2–7.4 (m, 3H), 7.6 (s, 1H), 8.1 (s, 1H).

MS (thermospray): M/Z (MH$^+$) 317.6; C$_{20}$H$_{32}$N$_2$O+H requires 317.3.

Example 30

1-Hexyl-3,4-dimethyl-4-(3-acetylphenyl)piperidine

To a solution of 1-hexyl-3,4-dimethyl-4-(3-cyanophenyl) piperidine (Example 1, 791 mg, 2.65 mmol) in anhydrous tetrahydrofuran (6 mL) at 0° C. was added methyl lithium (2.46 mL, 3.45 mmol) and the mixture darkened. The solution was then warmed to room temperature and stirred under a nitrogen atmosphere for 1 hour before being poured onto water (10 mL). The basic aqueous layer was extracted with diethyl ether:ethyl acetate (1:1, 3×10 mL). The combined organic extracts were dried (MgSO$_4$) and concentrated in vacuo. This gave the crude title compound as a colourless oil (720 mg, 86%).

NMR (CDCl$_3$): 0.75 (d, 3H), 0.9 (m, 3H), 1.2–1.4 (m, 9H), 1.4–1.55 (m, 2H), 1.65 (m, .H), 2.05 (m, 1H), 2.2–2.45 (m, 4H), 2.45–2.6 (m, 2H), 2.6 (s, 3H), 2.85 (m, 1H), 7.4 (t, 1H), 7.5 (d, 1H), 7.75 (d, 1H), 7.95 (s, 1H).

MS (thermospray): M/Z (MH$^+$) 316.3; C$_{21}$H$_{33}$NO+H requires 316.3.

Example 31

1-Hexyl-3,4-dimethyl-4-(3-ethynylphenyl)piperidine

A solution of 1-hexyl-3,4-dimethyl-4-{3-[2-(trimethylsilyl)ethynyl]-phenyl}piperidine (Preparation 4, 150 mg, 0.40 mmol) in tetrahydrofuran (2 mL) was cooled to -70° C. and tetrabutylammonium fluoride (1.0 M in THF, 0.41 mL, 0.41 mmol) was added slowly. The reaction mixture was allowed to warm to room temperature gradually before being diluted with dichloromethane (10 mL) and water (10 mL). The phases were separated and the aqueous layer was further extracted with dichloromethane (2×10 mL). The combined organics were dried (Na$_2$SO$_4$) and the solvent evaporated in vacuo. The oily yellow residue was purified by column chromatography on silica gel (10 g) eluted with ethyl acetate:hexane 0.880 ammonia (10:89:1) to give the title compound as an oil (100 mg).

NMR (CDCl$_3$): 0.75 (d, 3H), 0.9 (m, 3H), 1.2–1.35 (m, 9H), 1.35–1.55 (m, 2H), 1.6 (m, 1H), 2.0 (m, 1H), 2.2–2.6 (m, 6H), 2.8 (m, 1H), 3.05 (s, 1H), 7.2–7.35 (m, 3H), 7.45 (s, 1H).

MS (APCI): M/Z (MH$^+$) 298.6; C$_{21}$H$_{31}$N+H requires 298.3.

Example 32

1-Hexyl-3,4-dimethyl-4-(3-(1,1-dimethyl) hydroxymethylphenyl)piperidine

A solution of 1-hexyl-3,4-dimethyl-4-(3-methoxycarbonylphenyl)-piperidine (Example 3, 50 mg, 0.15 mmol) in anhydrous tetrahydrofuran was de-oxygenated by evacuating and flushing with nitrogen three times. The solution was then cooled to 0° C. and treated with methylmagnesium chloride (0.5 mL, 1.5 mmol, 3.0 M in tetrahydrofuran) dropwise. The reaction mixture was stirred at 50° C. for 2 hours and then saturated aqueous ammonium chloride solution (20 mL) was added followed by saturated aqueous sodium hydrogencarbonate (20 mL). The mixture was extracted with ethyl acetate (3×15 mL) and the combined organic phases were dried (MgSO$_4$) and concentrated in vacuo to give an oil (39 mg). The residue was purified by column chromatography on silica gel (1 g) eluted with a gradient of ethyl acetate:hexane:ammonia (50:50:1 to 25:75:1) to give the title compound as a colourless oil (30 mg).

NMR (CDCl$_3$, selected data): 0.75 (d, 3H), 0.9 (m, 3H), 1.25–1.4 (m, 9H), 1.4–1.55 (m, 2H), 1.6 (s, 61H), 1.65 (m, 1H), 2.05 (m, 11H), 2.2–2.45 (m, 41H), 2.45–2.65 (m, 2H), 2.8 (m, 1H), 7.15 (m, 1H), 7.2–7.3 (m, 2H), 7.45 (s, 1H).

MS (APCI): M/Z (MH$^+$) 332.4; C$_{22}$H$_{37}$NO+H requires 332.3.

Example 33

1-Hexyl-3,4-dimethyl-4-(3-hydroxymethylphenyl)-piperidine

A stirred solution of 1-hexanoyl-3,4-dimethyl-4-(3-methoxycarbonyl-phenyl)piperidine (Preparation 7, 80 mg, 0.23 mmol) in anhydrous tetrahydrofuran (1 mL) under nitrogen was treated with lithium aluminium hydride (1.0 M in ether, 0.70 mL, 0.70 mmol) and the mixture was stirred at room temperature for 3 hours. The reaction mixture was then quenched with water (7.5 mL) and extracted with ethyl acetate (7 mL). The phases were separated and the aqueous layer was further extracted with ethyl acetate (2×5 mL). The combined organics were dried (Na$_2$SO$_4$) and the solvent removed in vacuo to give the title compound as a pale oil (30 mg).

NMR (CDCl$_3$, selected data): 0.75 (d, 3H), 0.9 (m, 3H), 1.2–1.4 (m, 9H), 1.4–1.55 (m, 2H), 1.65 (m, 1H), 2.0 (m, 1H), 2.2–2.45 (m, 4H), 2.45–2.65 (m, 2H), 2.8 (m, 1M, 4.7 (s, 21), 7.1–7.35 (m, 41H).

MS (thermospray): M/Z (MH$^+$) 304.3; C$_{20}$H$_{33}$NO+H requires 304.3.

Example 34

1-Hexyl-3,4-dimethyl-4-(3-(2-hydroxyethyl)phenyl)-piperidine

To a stirred solution of 1-hexanoyl-3,4-dimethyl-4-(3-vinylphenyl)-piperidine (Preparation 8, 50 mg, 0.16 mmol) in bis(2-methoxyethyl)ether (1.5 mL) at 0° C. under nitrogen was added dropwise borane (1.0 M in tetrahydrofuran, 0.35 mL, 0.35 mmol). The reaction mixture was stirred at 0° C. for 30 minutes and then for 2 hours at room temperature. Trimethylamine N-oxide (48 mg, 0.64 mmol) was subsequently added and the reaction mixture heated at reflux under a nitrogen atmosphere for 2 hours. To the cooled reaction was then added diethyl ether (10 mL) and saturated aqueous sodium chloride solution (10 mL). The phases were separated and the aqueous layer was further extracted with diethyl ether (10 mL). The combined organics were dried (MgSO$_4$) and concentrated in vacuo. The residue was purified by column chromatography on silica gel (1.5 g) eluted with ethyl acetate:hexane (50:50) to give the title compound as an oil (30 mg).

NMR (CDCl$_3$, selected data): 0.75 (d, 3H), 0.9 (m, 3H), 1.25–1.4 (m, 9H), 1.4–1.55 (m, 2H), 1.6 (m, 1H), 2.0 (m, 1H), 2.2–2.45 (m, 4H), 2.45–2.6 (m, 2H), 2.8 (m, 1H), 2.85 (t, 2H), 3.85 (t, 2H), 7.05 (d, 1H), 7.1–7.35 (m, 3H).

MS (APCI): M/Z (MH$^+$) 318.6; C$_{21}$H$_{35}$NO+H requires 318.3.

Example 35

1-Hexyl-3,4-dimethyl-4-(3-(1-hydroxy-2-methylamino)-ethylphenyl)piperidine

To a solution of 1-hexanoyl-3,4-dimethyl-4-{3-[4-(4-methylphenyl)-sulfonyl-4,5-dihydro-1,3-oxazol-5-yl]phenyl}piperidine (Preparation 10, 345 mg, 0.68 mmol) in anhydrous tetrahydrofuran (5 mL) at room temperature was added lithium aluminium hydride (1.0 M solution in tetrahydrofuran, 0.74 mL, 0.74 mmol) dropwise over five minutes. The solution was stirred at room temperature under a nitrogen atmosphere for 2 hours and then cooled to 0° C. The reaction was quenched cautiously by the addition of aqueous sodium hydroxide solution (1.0 mL, 1.0 N) and then ethyl acetate (20 mL) and solid sodium hydrogencarbonate (excess) were added. The mixture was stirred vigorously for 30 minutes and then filtered through Celite®, washing with ethyl acetate. The filtrate was concentrated in vacuo and the residue was purified by column chromatography on silica gel eluted with neat ethyl acetate and then ethyl acetate-:methanol:0.880 ammonia (70:30:1) to give the title compound as a clear gum (120 mg).

NMR (CDCl$_3$, selected data): 0.75 (d, 3H), 0.9 (t, 3H), 1.2–1.4 (m, 9H), 1.4–1.55 (m, 2H), 1.6 (m, 1H), 2.0 (m, 1H), 2.2–2.6 (m, 9H), 2.65–2.85 (m, 3H), 4.75 (m, 1H), 7.1–7.35 (m, 4H).

MS (thermospray): M/Z (MH$^+$) 347.3; C$_{22}$H$_{38}$N$_2$O+H requires 347.3.

Preparation of Starting Materials

Preparation 1

1-Hexyl-3,4-dimethyl-4-(3-trifluoromethanesulfonyloxyphenyl)piperidine

To a solution of 1-hexyl-3,4-dimethyl-4-(3-hydroxyphenyl)piperidine (3.5 g, 12 mmol, *J. Med. Chem.*, 1993, 36, 2833) in dichloromethane (15 mL) was added triethylamine (3 mL) followed by N-phenyltrifluoromethanesulfonimide(6.1 g, 18 mmol) portionwise. The reaction mixture was stirred under nitrogen at room temperature for 18 hours then it was washed with aqueous sodium hydroxide solution (60 mL of 2 N). The separated aqueous layer was back-washed with dichloromethane (2×30 mL), after which the combined organics were dried (Na$_2$SO$_4$) and the solvent removed in vacuo to give a yellow oil. This was purified by column chromatography on silica gel (150 g) eluted with hexane:ethyl acetate:0.880 ammonia (66:33:1) to give the title compound as a yellow oil (4.22 g).

NMR (CDCl$_3$): 0.75 (d, 3H), 0.9 (m, 3H), 1.2–1.4 (m, 9H), 1.4–1.7 (m, 3H), 2.0 (m, 1H), 2.2–2.45 (m, 4H), 2.45–2.65 (m, 2H), 2.8 (m, 1H), 7.1 (d, 1H), 7.15 (s, 1H), 7.25–7.45 (m, 2H).

MS (thermospray): M/Z (MH$^+$) 422.3; C$_{20}$H$_{30}$F$_3$NO$_3$S+H requires 422.2.

Preparation 2

1-Benzyl-3,4-dimethyl-4-(3-trifluoromethanesulfonyloxyphenyl)piperidine

To a stirred solution of 1-benzyl-3,4-dimethyl-4-(3-hydroxyphenyl)-piperidine (10.16 g, 34.4 mmol, *J. Med.*

Chem., 1993, 36, 2833) in anhydrous dichloromethane (100 mL) was added triethylamine (8 mL) and the resulting solution was de-oxygenated by evacuating and flushing with nitrogen three times. N-Phenyltrifluoromethanesulfonimide (18.43 g, 51.6 mmol) was added and the mixture was de-oxygenated again, using the same procedure as before, and stirred overnight at room temperature under nitrogen. The reaction mixture was then diluted with dichloromethane (200 mL) and washed with aqueous sodium hydroxide solution (200 mL of 1 M). The aqueous phase was back-washed with dichloromethane (2×100 mL). The combined organics were dried ($Na_2SO_4$) and concentrated in vacuo to give an orange oil (ca 20 g) which was purified by column chromatography on silica gel (700 g) eluted with a gradient of ethyl acetate:hexane:0.880 ammonia (10:190:1 to 10:90:1). This gave the title compound as a colourless oil (13.98 g).

NMR ($CDCl_3$): 0.75 (d, 3H), 1.35 (s, 3H), 1.55 (m, 1H), 1.95 (m, 1H), 2.25–2.5 (m, 2H), 2.5–2.65 (m, 2H), 2.85 (m, 1H), 3.45 (d, 1H), 3.6 (d, 1H), 7.1 (d, 1H), 7.15 (s, 1H), 7.2–7.45 (m, 7H).

MS (thermospray): M/Z ($MH^+$) 428.0; $C_{21}H_{24}F_3NO_3S+H$ requires 428.2.

Preparation 3

3,4-Dimethyl-4-(3-(N-ethyl)amidophenyl)piperidine

To a solution of 1-benzyl-3,4-dimethyl-4-(3-(N-ethyl)amidophenyl)-piperidine (Example 16, 800 mg, 2.3 mmol) in methanol (40 mL) was added palladium on activated carbon (150 mg, Degussa type E101 NE/W, Pd 10% dry weight, ca 50% water). The resulting suspension was stirred at room temperature under an atmosphere of hydrogen at 415 kPa for 1½ days. It was then filtered through Celite® to remove the catalyst residues and concentrated in vacuo to give a foam (610 mg). Purification by column chromatography on silica gel (30 g) eluted with $CH_2Cl_2$:EtOH 0.880 ammonia (50:8:1) gave the title compound as a thick gum (557 mg).

NMR ($CDCl_3$, selected data): 0.7 (d, 3H),1.25 (t, 3H), 1.4 (s, 3H), 1.95 (m, 1H), 2.15 (m, 1H), 2.75 (m, 1H), 2.95–3.15 (m, 2H), 3.25 (m, 1H), 3.5 (m, 2H), 7.3–7.45 (m, 2H), 7.5 (d, 1H), 7.7 (s, 1H).

MS (APCI): M/Z ($MH^+$) 261.5; $C_{16}H_{24}N_2O+H$ requires 261.2.

Preparation 4

1-Hexyl-3,4-dimethyl-4-{3-[2-(trimethylsilyl)ethynyl]-phenyl}piperidine

To a solution of 1-hexyl-3,4-dimethyl-4-(3-trifluoromethanesulfonyloxyphenyl)piperidine (Preparation 1, 350 mg, 0.83 mmol) in tetrahydrofuran (12 mL) was added diisopropylamine (4 mL) and trimethylsilylethyne (4.5 g, 46 mmol) and the mixture was de-oxygenated by evacuating and flushing with nitrogen five times. Copper(I) iodide (6.2 mg 0.033 mmol), and then catalytic quantities of palladium(II) acetate and 1,1 '-bis(diphenylphosphino) ferrocene were added. The reaction mixture was heated to reflux under nitrogen for 8 hours, before being allowed to cool to room temperature. Water (10 mL) and dichloromethane (10 mL) were added, the phases separated and the aqueous layer further extracted with dichloromethane (2×10 mL). The combined organics were then dried ($Na_2SO_4$) and the solvent removed in vacuo. The residual brown oil was purified by column chromatography on silica gel (25 g) eluted with a gradient of ethyl acetate:hexane:0.880 ammonia (20:79:1 to 50:49:1) to give the title compound as an oil (150 mg).

NMR ($CDCl_3$): 0.25 (s, 9H), 0.75 (d, 3H), 0.9 (m, 3H), 1.2–1.4 (m, 9H), 1.4–1.55 (m, 2H), 1.6 (m, 1H), 2.0 (m, 1H), 2.2–2.4 (m, 4H), 2.4–2.6 (m, 2H), 2.8 (m, 1H), 7.2–7.35 (m, 3H), 7.4 (s, 1H).

MS (thermospray): M/Z ($MH^+$) 370.4; $C_{24}H_{39}NSi+H$ requires 370.3.

Preparation 5

1-Hexanoyl-3,4-dimethyl-4-(3-hydroxyphenyl)-piperidine

To a stirred solution of 3,4-dimethyl-4-(3-hydroxyphenyl) piperidine (3.8 g, 18.6 mmol, J. Org. Chem., 1991, 56, 1660) in dichloromethane (30 mL) at 0° C. was added triethylamine (3.9 mL, 27.8 mmol) followed by the dropwise addition of hexanoic anhydride (4.7 mL, 20.4 mmol) over 5 minutes. The reaction was stirred under a nitrogen atmosphere for 3 hours at room temperature and then quenched by the addition of saturated aqueous sodium hydrogencarbonate (50 mL). The two layers were separated and the aqueous layer was extracted with dichloromethane (3×50 mL). The combined organic layers were dried ($MgSO_4$) and concentrated in vacuo. The residue was purified by column chromatography on silica gel eluting with ethyl acetate:hexane (1:1). The title compound was obtained as a clear oil (4.5 g).

NMR ($CDCl_3$, selected data from a 13:9 mixture of rotamers): 0.65 (d, 3H), 0.9 (m, 3H), 1.25–1.45 (m, 7H), 1.55–1.75 (m, 3H), 2.05 (m, 1H), 2.15 (m, 1H), 2.25–2.55 (m, 2H), 2.95 (m, 0.59H), 3.15 (m, 0.41H), 3.35 (m, 0.41H), 3.5–3.7 (m, 1.18H), 3.85 (m, 0.41H), 4.4 (m, 0.41H), 4.75 (m, 0.59H), 6.7 (d, 1H), 6.75–6.85 (m, 2H), 7.15 (t, 1H).

MS (thermospray): M/Z ($MH^+$) 304.1; $C_{19}H_{29}NO_2+H$ requires 304.2.

Preparation 6

1-Hexanoyl-3,4-dimethyl-4-(trifluoromethanesulfonyloxyphenyl)piperidine

To a stirred solution of 1-hexanoyl-3,4-dimethyl-4-(3-hydroxyphenyl)-piperidine (Preparation 5, 3.1 g, 10.1 mmol) in dichloromethane (30 mL) at room temperature was added triethylamine (2.82 mL, 20.2 mmol) followed by N-phenyltrifluoromethanesulfonimide (3.6 g, 15.1 mmol) portionwise. The reaction was stirred under a nitrogen atmosphere at room temperature for 16 hours and then aqueous sodium hydroxide (30 mL of 2 N) was added. The bi-phasic mixture was stirred vigorously for 2 hours before the two layers were separated and the aqueous layer extracted with dichloromethane (3×20 mL). The combined organic layers were dried ($MgSO_4$) and concentrated in vacuo. The residue was purified by column chromatography on silica gel eluting with a gradient of ethyl acetate:hexane (1:2 and then 2:1). The title compound was obtained as a clear oil (3.6 g).

NMR ($CDCl_3$, selected data from a 7:5 mixture of rotamers): 0.55–0.65 (m, 3H), 0.85–0.95(m, 3H), 1.25–1.4 (m, 4H), 1.45 (s, 3H), 1.55–1.75 (m, 3H), 2.0–2.5 (m, 4H), 2.9 (m, 0.58H), 3.15 (m, 0.42H), 3.35 (m, 0.42H), 3.6 (m, 1.16H), 3.9 (m, 0.42H), 4.4 (m, 0.42H), 4.75 (m, 0.58H), 7.05–7.15 (m, 2H), 7.3 (m, 1H), 7.4 (m, 1H).

MS (thermospray): M/Z ($MH^+$) 436.4; $C_{20}H_{28}F_3NO_4S+H$ requires 436.2.

Preparation 7

1-Hexanoyl-3,4-dimethyl-4-(3-methoxycarbonylphenyl)-piperidine

To a solution of 1-hexanoyl-3,4-dimethyl-4-(trifluoromethanesulfonyloxyphenyl)piperidine (Preparation 6, 267 mg, 0.48 mmol) in anhydrous N,N-dimethylformamide (2 mL) was added triethylamine (0.18 mL) and methanol (0.4 mL). The mixture was de-oxygenated by evacuating and flushing with nitrogen five times. Palladium(II) acetate (4.4 mg) and 1,1'-bis(diphenylphosphino)ferrocene (8 mg) were added and the solution was purged with carbon monoxide. The reaction mixture was heated to 60° C. under an atmosphere of carbon monoxide for 7 hours then it was cooled to room temperature and diluted with saturated aqueous sodium chloride solution (10 mL). The phases were separated and the aqueous layer was extracted with dichloromethane (4×15 mL). The combined organics were dried ($Na_2SO_4$) and concentrated in vacuo. The residue was purified by column chromatography on silica gel (50 g) eluted with hexane:ethyl acetate:0.880 ammonia (66:33:1). The title compound was obtained as a pale yellow oil (110 mg).

NMR ($CDCl_3$, selected data from a 9:7 mixture of rotamers): 0.55–0.7 (m, 3H), 0.85–0.95 (m, 3H), 1.25–1.4 (m, 4H), 1.45 (s, 3H), 1.6–1.8 (m, 3H), 2.05–2.45 (m, 4H), 2.9 (m, 0.56H), 3.15 (m, 0.44H), 3.4 (m, 0.44H), 3.6 (m, 1.12H), 3.9 (m, 0.44H), 3.95 (s, 3H), 4.4 (0.44H), 4.7 (m, 0.56H), 7.35–7.5 (m, 2H), 7.9 (m, 1H), 7.95 (m, 1H).

MS (thermospray): M/Z (MH$^+$) 346.3; $C_{21}H_{31}NO_3$+H requires 346.2.

Preparation 8

1-Hexanoyl-3,4-dimethyl-4-(3-vinylphenyl)piperidine

To a stirred solution of 1-hexanoyl-3,4-dimethyl-4-(trifluoromethanesulfonyloxyphenyl)piperidine (Preparation 6, 3.0 g, 6.90 mmol) in tetrahydrofuran (30 mL) at room temperature were added sequentially vinyltributyltin (2.12 mL, 7.24 mmol), lithium chloride (585 mg, 13.8 mmol), and tetrakis(triphenylphosphine)palladium(0) (80 mg, 0.69 mmol). The mixture was heated to reflux under a nitrogen atmosphere for 1½ hours at which time a few crystals of 4-tert-butylcatechol were added. Heating at reflux was then continued for a further 16 hours. The mixture was cooled and concentrated in vacuo. The residue was purified by column chromatography on silica gel eluting with a gradient of ethyl acetate:hexane (1:10 to 1:3). The title compound was obtained as a clear oil (2.1 g).

NMR ($CDCl_3$, selected data from a 5:4 mixture of rotamers): 0.55–0.7 (m, 3H), 0.85–1.0 (m, 3H), 1.25–1.4 (m, 4H), 1.4 (s, 3H), 1.6–1.75 (m, 3H), 2.05–2.45 (m, 4H), 2.9 (m, 0.56H), 3.15 (m, 0.44H), 3.35 (m, 0.44H), 3.6 (m, 1.12H), 3.9 (m, 0.44H), 4.4 (m, 0.44H), 4.7 (m, 0.56H), 5.25 (d, 1H), 5.75 (d, 1H), 6.7 (dd, 1H), 7.15 (m, 1H), 7.2–7.35 (m, 31H).

MS (APCI): M/Z (MH$^+$) 314.5; $C_{21}H_{31}NO$+H requires 314.2.

Preparation 9

1-Hexanoyl-3,4-dimethyl-4-(3-formylphenyl)piperidine

To a solution of 1-hexanoyl-3,4-dimethyl-4-(3-vinylphenyl)piperidine (Preparation 8, 2.4 g, 7.67 mmol) in acetone (20 mL) at room temperature was added water (5 mL), 4-methylmorpholine N-oxide (1.1 g, 9.20 mmol) and finally osmium tetroxide (3.83 mL, 2.5 wt % solution in tert-butanol). The yellow solution was stirred at room temperature for 1 hour and then sodium periodate (4.92 g, 23.0 mmol) was added in one portion. After stirring the reaction for 3 hours a heavy precipitate had developed and the reaction mixture was filtered through Celite®, washing with acetone. The filtrate was concentrated in vacuo, the crude oil was dissolved in dichloromethane, dried ($MgSO_4$) and concentrated in vacuo. The residue was purified by column chromatography on silica gel eluting with ethyl acetate:hexane (1:1). The title compound was isolated as clear oil (2.0 g).

NMR ($CDCl_3$, selected data from a 1:1 mixture of rotamers): 0.55–0.7 (m, 3H), 0.85–0.95 (m, 3H), 1.25–1.4 (m, 4H), 1.45 (s, 3H), 1.55–1.8 (m, 3H), 2.1–2.5 (m, 4H), 2.95 (m, 0.5H), 3.15 (m, 0.5H), 3.4 (m, 0.5H), 3.6 (m, 1H), 3.9 (m, 0.5H), 4.4 (m, 0.5H), 4.75 (m, 0.5H), 7.45-7.6 (m, 2H), 7.7 (m, 1H), 7.75 (m, 11H), 10.0 (s, 1H).

MS (thermospray): M/Z (MH$^+$) 316.3; $C_{20}H_{29}NO_2$+H requires 316.2.

Preparation 10

1-Hexanoyl-3,4-dimethyl-4-{3-[4-(4-methylphenyl)-sulfonyl-4,5-dihydro-1,3-oxazol-5-yl]phenyl}piperidine To a solution of 1-hexanoyl-3,4-dimethyl-4-(3-formylphenyl)piperidine (Preparation 9, 758 mg, 2.40 mmol) in ethanol (20 mL) was added [(4-methylphenyl)sulfonyl]methyl isocyanide (460 mg, 2.34 mmol) followed by sodium cyanide (12 mg, 0.24 mmol). The mixture was stirred at room temperature under a nitrogen atmosphere for five hours and then concentrated in vacuo. The residue was purified by column chromatography on silica gel using a gradient elution of hexane:ethyl acetate (67:33 to 0:100). The title compound was isolated as a clear oil (909 mg).

NMR ($CDCl_3$) (selected data from a 1:1 mixture of rotamers): 0.55–0.65 (m, 3H), 0.85–0.95 (m, 3H), 1.25–1.45 (m, 7H), 1.55–1.75 (m, 3H), 2.05–2.45 (m, 4H), 2.45 (s, 3H), 2.9 (m, 0.51H), 3.15 (m, 0.5H), 3.35 (m, 0.5H), 3.6 (m, 11H), 3.9 (m, 0.51H), 4.4 (m, 0.51H), 4.7 (m, 0.51H), 5.0 (d, 1H), 6.05 (d, 1H), 7.1–7.3 (m, 41H), 7.3–7.45 (m, 31H), 7.85 (d, 2H).

MS (thermospray) M/Z (MH$^+$) 511.1; $C_{29}H_{38}N_2O_4S$+H requires 511.3.

Biological Activity

The Ki values of certain compounds of the present invention in the opioid receptor binding assays were determined, and the compounds of Examples 4, 8, 18 and 20 were all found to have Ki values of 4000 nM or less for the $\mu$ receptor. The compounds of the invention also possess affinity at the δ and κ opioid receptors.

What is claimed is:

1. A compound of formula I,

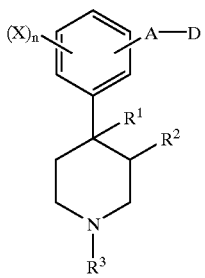

wherein A represents a single bond, D represents $C(O)N(R^4)(R^5)$;

$R^4$ and $R^5$ independently represent H, $C_{1-6}$ alkyl, $C_{3-8}$ cycloalkyl, aryl, $C_{1-4}$ alkylphenyl, which latter four groups are optionally substituted by one or more substituents selected from nitro, halo, $C_{1-4}$ alkyl and $C_{1-4}$ alkoxy (which latter two groups are optionally substituted by one or more halo atoms), or $R^4$ and $R^5$, together with the N-atom to which they are attached, form a 4- to 7-membered heterocyclic ring, which ring optionally contains one or more additional heteroatoms selected from oxygen, nitrogen and sulfur and which ring is optionally substituted by one or more substituents selected from $C_{1-4}$ alkyl, $C_{1-4}$ alkoxy, OH, =O, nitro, amino and halo;

$R^1$ and $R^2$ are each independently H or $C_{1-4}$ alkyl;

$R^3$ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{11a})(R^{11b})$), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{11c}$, $S(O)_pR^{11d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{12a})S(O)_2R^{13}$, $Het^1$, aryl, or adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms));

p is 0, 1 or 2;

$R^{11a}$ to $R^{11d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{11d}$ does not represent H when p represents 1 or 2;

$R^{12a}$ is H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$;

$R^{13}$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

$Het^1$, $Het^2$ and $Het^3$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

X is H, halo, $C_{1-4}$ alkyl or $C_{1-4}$ alkoxy (which latter two groups are optionally substituted by one or more halo atoms);

n is 0, 1 or 2;

or pharmaceutically, or veterinarily, acceptable derivatives thereof.

2. A compound as claimed in claim 1 wherein the group A–D is attached in the meta-position relative to the piperidine ring.

3. A compound as claimed in claim 1 wherein $R^1$ represents $C_{1-2}$ alkyl.

4. A compound as claimed in claim 1 wherein $R^2$ represents H or $C_{1-2}$ alkyl.

5. A compound as claimed in claim 1 wherein $R^3$ represents saturated $C_{1-10}$ alkyl, optionally substituted by one or more substituents selected from $OR^{11c}$, CN, halo, $C_{2-4}$ alkanoyl, $C_{1-4}$ alkoxy carbonyl, $N(R^{12a})SO_2R^{13}$, $Het^1$, and aryl (which latter group is optionally substituted by one or more substituents selected from OH, $C_{1-4}$ alkyl, $C_{1-4}$ alkoxy, $C_{2-5}$ alkanoyl, halo, nitro, amino, CN and $CONH_2$).

6. A compound as claimed in claim 1 wherein $R^{11c}$ represents H, $C_{1-6}$ alkyl or aryl (which latter groups is optionally substituted by one or more substituents selected from OH, $C_{1-4}$ alkyl, $C_{1-4}$ alkoxy, $C_{2-5}$ alkanoyl, halo, nitro, amino, CN and $CONH_2$); and $R^{12a}$ is H, $C_{1-4}$ alkyl, $C_{1-2}$ alkylphenyl or aryl (which latter three groups are optionally substituted by one or more substituents selected from halo, $C_{1-4}$ alkyl $C_{1-4}$ alkoxy).

7. A compound as claimed in claim 1 wherein $R^3$ represents $C_{1-4}$ alkyl, $C_{1-2}$ alkylphenyl or aryl (which three groups are all optionally substituted by one or more substituents selected from halo, $C_{1-4}$ alkyl and $C_{1-4}$ alkoxy).

8. A compound as claimed in claim 1 wherein $R^4$ and $R^5$ independently represent H, $C_{1-4}$ alkyl or $C_{1-3}$ alkylphenyl, which latter two groups are optionally substituted by $C_{1-4}$ alkoxy.

9. A compound as claimed in claim 1 wherein $R^3$ represents saturated $C_{1-7}$ alkyl, optionally substituted by one or more substituents selected from CN, O—($C_{1-6}$ alkyl), phenyl, or O-(phenyl).

10. A compound as claimed in claim 1 wherein X represents halo.

11. A compound as claimed in claim 1 wherein n represents 0 or 1.

12. A pharmaceutical composition comprising a pharmaceutically effective amount of a compound as defined in any one of claims 1 to 11, in admixture with a pharmaceutically, or a veterinarily, acceptable adjuvant, diluent or carrier.

13. The pharmaceutical composition as claimed in claim 12, which is a veterinary formulation.

14. A process for the preparation of a compound of the formula

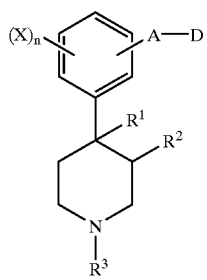

I wherein A represents a single bond;

D represents C(O)N(R⁴)(R⁵);

R⁴ and R⁵ independently represent H, $C_{1-6}$ alkyl, $C_{3-8}$ cycloalkyl, aryl, $C_{1-4}$ alkylphenyl, which latter four groups are optionally substituted by one or more substituents selected from nitro, halo, $C_{1-4}$ alkyl and $C_{1-4}$ alkoxy (which latter two groups are optionally substituted by one or more halo atoms), or R⁴ and R⁵, together with the N-atom to which they are attached, form a 4- to 7-membered heterocyclic ring, which ring optionally contains one or more additional heteroatoms selected from oxygen, nitrogen and sulfur and which ring is optionally substituted by one or more substituents selected from $C_{1-4}$ alkyl, $C_{1-4}$ alkoxy, OH, =O, nitro, amino and halo;

R¹ and R² are each independently H or $C_{1-4}$ alkyl;

R³ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —N(R$^{11a}$)(R$^{11b}$)), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from OR$^{11c}$, S(O)$_p$R$^{11d}$, CN, halo, $C_{1-6}$ alkoxy carbonyl, $C_{1-6}$ alkanoyl, $C_{2-6}$ alkanoyloxy, $C_{3-8}$ cycloalkyl, $C_{4-9}$ cycloalkanoyl, N(R$^{12a}$)S(O)$_2$R$^{13}$, Het¹, aryl, or adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms));

p is 0, 1 or 2;

R$^{11a}$ to R$^{11d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or Het²;

provided that R$^{11d}$ does not represent H when p represents 1 or 2;

R$^{12a}$ is H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_{1-4}$ alkyl.

$C_{1-4}$ alkoxy and $C_{1-5}$ alkanoyl (which latter three groups are optionally substituted by one or more halo atoms)), or Het³;

R¹³ represents $C_{1-4}$ alkyl, $C_{3-8}$ cycloalkyl, $C_{1-4}$ alkylphenyl or aryl, which four groups are optionally substituted by or one or more substituents selected from $C_{1-4}$ alkyl alkoxy, OH, nitro, amino or halo;

Het¹, Het² and Het³ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

X is H, halo, $C_{1-4}$ alkyl or $C_{1-4}$ alkoxy (which latter two groups are optionally substituted by one or more halo atoms);

n is 0, 1 or 2;

or pharmaceutically, or veterinarily, acceptable derivatives thereof which process comprises:

a) for compounds of formula I in which D represents C(O)NH₂, controlled hydrolysis of

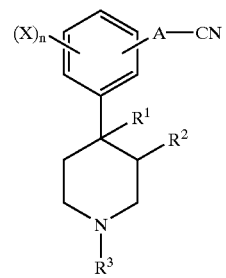

A) reaction of a compound of the formula

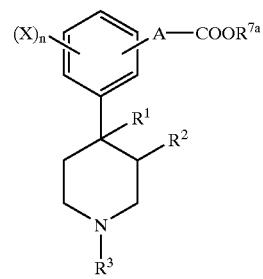

is with a compound of formula XI,

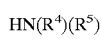

XI or an acid addition salt thereof, wherein R$^{7a}$ is $C_{1-4}$ alkyl, $C_{3-8}$ cycloalkyl, aryl or $C_{1-4}$ alkylphenyl, which latter four groups are optionally, substituted by one or more substituents from alkyl and $C_{1-4}$ alkoxy (which latter two groups are optionally substituted by one or more halo atoms); or B) reaction of a compound of the formula

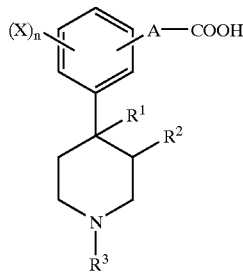

with a compound of formula XI, as defined above.

c) for compounds of formula I wherein $R^3$ represents $C_1$ alkyl optionally substituted by $C_{3-8}$ cycloalkyl, $Het^1$, aryl, or adamantyl, (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents optionally substituted $C_{2-10}$ alkyl, $C_{3-10}$ alkenyl or $C_{3-10}$ alkynyl which alkyl, alkenyl or alkynyl groups are attached to the piperidine nitrogen atom via a $CH_2$ group, reduction of a corresponding compound of formula XIX,

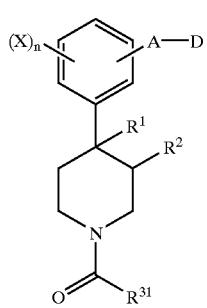

XIX wherein $R^{31}$ represents H, $C_{3-8}$ cycloalkyl, $Het^1$, aryl, adamantyl, (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{11c}$, $S(O)_pR^{11d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{12a})S(O)_2R^{13}$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms));

d) reaction of a corresponding compound of formula XX,

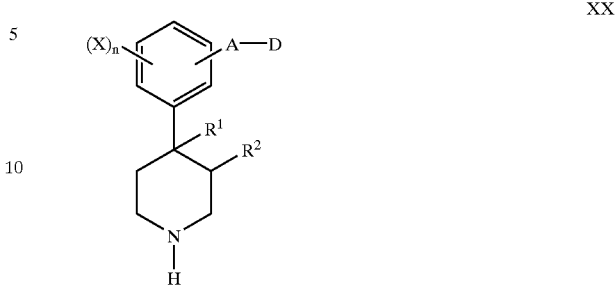

XX with a compound of formula VIII,

$$R^3-L^1 \qquad \text{VIII}$$

wherein $L^1$ is a leaving group;

e) for compounds of formula I wherein $R^3$ represents $C_1$ alkyl, which, is optionally substituted by $R^{31}$, wherein $R^{31}$ is as defined above, reaction of a corresponding compound of formula XX, as defined above, with a compound of formula XXII,

$$R^{31}CHO \qquad \text{XXII}$$

in the presence of a reducing agent; or f) for compounds of formula I wherein $R^3$ is a $C_{1-10}$ alkyl, $C_{4-10}$ alkenyl or $C_{4-10}$ alkynyl group that is fully saturated from 1- to 3-C (relative to the piperidine N-atom), and which $R^3$ group is substituted at 2-C (relative to the piperidine N-atom) by $S(O)R^{11d}$, $S(O)_2R^{11d}$, alkanoyl, cycloalkanoyl, alkoxy carbonyl, or CN, reaction of a corresponding compound of formula XX, as defined above, with a compound of formula XXIII,

$$R^{3a}-Z \qquad \text{XXIII}$$

wherein $R^{3a}$ represents $R^{3a}$ is $C_{1-10}$ alkyl, alkenyl or $C_{3-10}$ alkynyl wherein said alkyl, alkenyl or alkynyl groups are optionally substituted and/or terminated by one or more substituents selected from $OR^{11c}$, $S(O)_pR^{11d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{12a})S(O)_2R^{13}$, $Het^1$, aryl, and adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms));

and the $R^{3a}$ chain contains an additional carbon-carbon double bond α,β to the Z-substituent, and Z represents $S(O)R^{11d}$, $S(O)_2R^{11d}$, alkanoyl, cycloalkanoyl, alkoxy carbonyl, or CN.

* * * * *